(12) United States Patent
Shi et al.

(10) Patent No.: US 6,903,133 B2
(45) Date of Patent: Jun. 7, 2005

(54) ANTICANCER COMPOUNDS

(75) Inventors: Qian Shi, Chapel Hill, NC (US); Hui-Kang Wang, Chapel Hill, NC (US); Masayoshi Oyama, Aichi Prefecture (JP); John Robert Vance, Chapel Hill, NC (US); Ming S. Chen, Cupertino, CA (US)

(73) Assignee: Plantaceutica, Inc., Research Triangle Park, NC (US)

( * ) Notice: Subject to any disclaimer, the term of this patent is extended or adjusted under 35 U.S.C. 154(b) by 15 days.

(21) Appl. No.: 10/685,870

(22) Filed: Oct. 14, 2003

(65) Prior Publication Data

US 2004/0138288 A1 Jul. 15, 2004

Related U.S. Application Data

(60) Provisional application No. 60/417,785, filed on Oct. 11, 2002.

(51) Int. Cl.[7] .................... A61K 31/36; C07D 407/02
(52) U.S. Cl. ........................ 514/463; 549/298
(58) Field of Search ............... 514/463; 549/298

(56) References Cited

U.S. PATENT DOCUMENTS

| | | | |
|---|---|---|---|
| 5,061,791 A | 10/1991 | Showalter et al. | 536/17.4 |
| 5,132,322 A | 7/1992 | Lee et al. | 514/468 |
| 5,300,500 A | 4/1994 | Lee et al. | 514/232 |
| 5,332,811 A | 7/1994 | Lee et al. | 544/148 |
| 5,338,867 A | 8/1994 | Choy et al. | 549/298 |
| 5,489,698 A | 2/1996 | Terada et al. | 549/298 |
| 5,541,223 A | 7/1996 | Lee et al. | 514/468 |
| 5,571,914 A | 11/1996 | Terada et al. | 544/148 |
| 6,051,721 A | 4/2000 | Berkowitz | 549/298 |
| 6,207,673 B1 | 3/2001 | Lee et al. | 514/280 |
| 2002/0082432 A1 | 6/2002 | Kamal et al. | 549/298 |

*Primary Examiner*—Taofiq Solola
(74) *Attorney, Agent, or Firm*—Fish & Richardson P.C.

(57) ABSTRACT

This invention features compounds having formula (I):

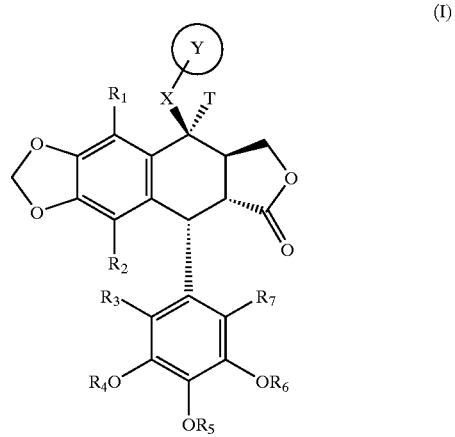

(I)

wherein, $R_1$, $R_2$, $R_3$, $R_4$, $R_5$, $R_6$, $R_7$, T, X, and Y are as defined herein. This invention also features a method for treating cancer. The method includes administrating to a subject in need thereof a compound of formula (I).

44 Claims, No Drawings

ANTICANCER COMPOUNDS

This application claims the benefit of prior U.S. prov. app. 60/417,785 filed Oct. 11, 2002.

BACKGROUND

Podophyllotoxin is a naturally occurring compound extracted from a mandrake plant. Some derivatives of podophyllotoxin, e.g., etoposide and teniposide, have been studied for use in chemotherapy for cancer. (See, e.g., Jardine (1980) *Anticancer Agents Based on Natural Products Models*; Academic Press: New York, p 319; Issell (1982) *Cancer Chemother. Pharmacol.* 7: 73; and Lee et al. (1995) *Food and Drug Analysis.* 3:209). These derivatives inhibit topoisomerase II by stabilizing a topoisomerase II-DNA complex in which the DNA is cleaved and remains covalently linked to the enzyme. This inhibition leads to cell death. See, e.g., Osheroff et al. (1991) *BioEssays* 13: 269; Alton & Harris (1993) *Br. J. Haematol.* 85: 241–245, Cho et al. (1996) *J. Med. Chem.* 39: 1383; MacDonald et al. (1991) *DNA Topoisomerase in Cancer*; Oxford University Press: New York. It is known that the aforementioned podophyllotoxin derivatives have several limitations such as development of drug resistance, myelo-suppression, and poor oral bioavailability. Thus, identification of novel compounds that also target topoisomerase II can lead to new therapeutics for treating or preventing cancer or symptoms associated with cancer.

SUMMARY

The present invention is based, in part, on the discovery of novel podophyllotoxin derivatives that possess anticancer activities.

In one aspect, this invention features compounds having formula (I) that includes a tetracyclic-fused ring:

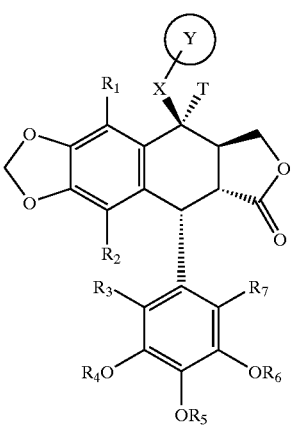

(I)

each of $R_1$, $R_2$, $R_3$ and $R_7$ independently is H or alkyl; each of $R_4$ and $R_6$ independently is alkyl; $R_5$ is H or $P(O)(OR_a)_2$, in which $R_a$ is H or alkyl; T is H, or together with X is =N; X is a bond, O, S, or $NR_b$, in which $R_b$ is H or alkyl; or together with T, is =N; and Y is 5-membered heteroaryl or heterocyclyl, each of which optionally substituted with one or more of halogen, alkyl, cyclyl, aryl, heteroaryl, heterocyclyl, $-OR_c$, $-NR_cR_c'$, $-SR_c$, $-CN$, $-NO_2$, $-SO_2R_c$, $-C(O)OR_c$, $-C(O)NR_cR_c'$, $-NHC(O)R_c$, $-(CH_2)_qOPO_3H_2$, $-CH_2C(O)NOR_c''$, and

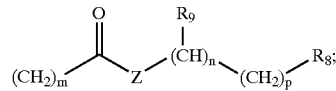

in which each of $R_c$ and $R_c'$ independently is H or alkyl; $R_c''$ is H, alkyl, or silyl; Z is O or NH; each of m and n independently is 0 or 1; p is 0, 1, or 2; q is 1, 2, 3, or 4; and each of $R_8$ and $R_9$ independently is H, alkyl, aryl, heteroaryl, heterocyclyl, $-OR_d$, $-NR_dR_d'$, $-SR_d$, $-CN$, $-NO_2$, $-SO_2R_d$—$C(O)OR_d$, $-C(O)NR_dR_d'$, $-NHC(O)R_d$, or $-NHC(O)OR_d$, in which each of $R_d$ and $R_d'$ independently is H or alkyl.

Referring to the just-described compounds, for a subset of these compounds X is NH and T is H. Another subset of the compounds are those wherein each of $R_1$, $R_2$, $R_3$, and $R_7$ is H; or each of $R_4$ and $R_6$ is methyl; or $R_5$ is H.

Further, another subset of the compounds are those wherein Y is heteroaryl substituted with

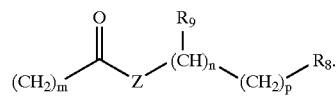

In some embodiments, m is 1. In these compounds, the heteroaryl can be

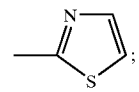

X can be NH; T can be H; each of $R_1$, $R_2$, $R_3$, and $R_7$ can be H; each of $R_4$ and $R_6$ can be methyl; and $R_5$ can be H. In other embodiments, m is 0.

Unless specifically pointed out, alkyl, alkenyl, aryl, heteroaryl, cyclyl, and heterocyclyl mentioned herein include both substituted and unsubstituted moieties. The term "substituted" refers to one or more substituents (which may be the same or different), each replacing a hydrogen atom. Examples of substituents include halogen, cyano, nitro, hydroxyl, amino, mercapto, alkyl, alkenyl, alkynyl, aryl, heteroaryl, cyclyl, heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein each of alkyl, alkenyl, aryl, heteroaryl, cyclyl, and heterocyclyl is optionally substituted with halogen, cyano, nitro, hydroxyl, amino, mercapto, alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

As used herein, the term "alkyl" refers to a straight-chained or branched alkyl group containing 1 to 6 carbon atoms. Examples of alkyl groups include methyl, ethyl, n-propyl, isopropyl, tert-butyl, and n-pentyl.

The term "alkenyl" refers to a straight-chained or branched alkenyl group containing 2 to 6 carbon atoms. Examples of alkenyl groups include vinyl, allyl (2-propenyl), dimethylallyl, and butenyl.

The term "aryl" refers to a hydrocarbon ring system (monocyclic to tricyclic) having at least one aromatic ring. Examples of aryl groups include, but are not limited to, phenyl, naphthyl, and anthracenyl.

The term "heteroaryl" refers to a hydrocarbon ring system (monocyclic to tricyclic) having at least one aromatic ring which contains at least one heteroatom (e.g., O, N, or S) as part of the ring in place of carbon atoms. Examples of heteroaryl groups include, but are not limited to, furyl, pyrrolyl, pyrazolyl, thiophenyl, thiadiazolyl, tetrazolyl, triazolyl, triazinyl, thienyl, oxazolyl, isoxazolyl, imidazolyl, thiazolyl, isothiazolyl, benzimidazolyl, pyridinyl, pyrimidinyl, quinazolinyl, indolyl, indiazolyl, isoindolyl, benzotriazolyl, purinyl, benzothiazolyl, benzoisothiazolyl, and benzothiadiazolyl.

The term "5-membered heteroaryl" refers to a ring system (monocyclic to tricyclic) containing at least one aromatic ring which has 5 ring atoms including one or more heteroatoms (e.g., O, N, or S). Examples of 5-membered heteroaryl include, but are not limited to, furyl, pyrrolyl, pyrazolyl, thiadiazolyl, tetrazolyl, triazolyl, thienyl, oxazolyl, isoxazolyl, imidazolyl, thiazolyl, isothiazolyl, benzimidazolyl, benzotriazolyl, purinyl, benzothiazolyl, benzoisothiazolyl, and benzothiadiazolyl.

The term "cyclyl" refers to a hydrocarbon ring system containing 3 to 8 carbon ring members. It includes saturated and unsaturated cycles. Examples of cyclyl groups include cyclopropyl, cyclobutyl, cyclopentyl, cyclohexyl, methylcyclohexyl, and cycloheptyl.

The term "heterocyclyl" refers to a hydrocarbon ring system containing 3 to 8 ring members that have at least one heteroatom (e.g., N, O, or S) as part of the ring in place of carbon atoms. It includes saturated and unsaturated heterocycles. Examples of heterocyclyl groups include, but are not limited to, piperidyl, morpholinyl, pyranyl, dioxanyl, and piperazinyl.

Set forth below are exemplary compounds of this invention.

Compounds 1–210 having the following formula:

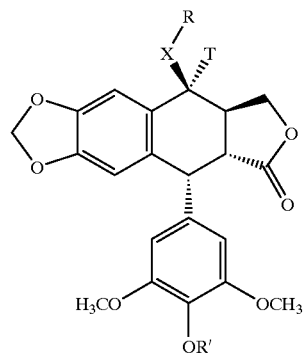

| Compound ID | R | X | T | R' |
|---|---|---|---|---|
| 1 | (2-methylthiazol-4-yl)CH₂C(O)NH-CH(CH₂-indol-3-yl)(CO₂CH₃) | NH | H | H |
| 2 | (2-methylthiazol-4-yl)CH₂C(O)NH-CH(CH₂-indol-3-yl)(COOC₂H₅) | NH | H | H |
| 3 | (6-methylpyridin-3-yl)C(O)NH-CH(COOC₂H₅)(CH₂-indol-3-yl) | NH | H | H |
| 4 | (3-methylpyrazin-2-yl)C(O)NH-CH(COOC₂H₅)(CH₂-indol-3-yl) | NH | H | H |

-continued

| Compound ID | R | X | T | R' |
|---|---|---|---|---|
| 5 | [3-methyl-1H-1,2,4-triazol-5-yl]CH₂C(O)NH–CH(COOC₂H₅)–(1H-indol-3-yl) | NH | H | H |
| 6 | [2-methylthiazol-4-yl]CH₂C(O)NH–CH₂–(1H-indol-3-yl) | NH | H | H |
| 7 | [2-methylthiazol-4-yl]CH₂C(O)NH–CH(CO₂CH₃)–(4-hydroxyphenyl) | NH | H | H |
| 8 | [2-methylthiazol-4-yl]CH₂C(O)NH–CH(CO₂C₂H₅)–(4-hydroxyphenyl) | NH | H | H |
| 9 | [2-methylthiazol-4-yl]CH₂C(O)NH–CH(COOH)–(4-hydroxyphenyl) | NH | H | H |
| 10 | [6-methylpyridin-3-yl]C(O)NH–CH(COOC₂H₅)–CH₂–(4-hydroxyphenyl) | NH | H | H |
| 11 | [2-methylthiazol-4-yl]CH₂C(O)NH–CH₂CH₂–(4-hydroxyphenyl) | NH | H | H |

-continued

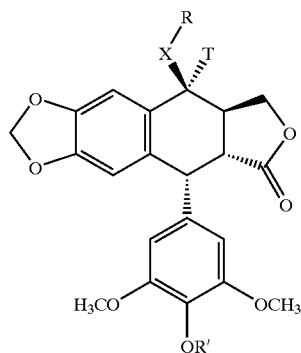

| Compound ID | R | X | T | R' |
|---|---|---|---|---|
| 12 | 2-methylthiazol-4-yl-CH2-C(O)NH-CH(CH2Ph)-CO2CH3 | NH | H | H |
| 13 | 2-methylthiazol-4-yl-CH2-C(O)NH-CH(CH2Ph)-CO2C2H5 | NH | H | H |
| 14 | 6-methylpyridin-3-yl-C(O)NH-CH(CH2Ph)-COOC2H5 | NH | H | H |
| 15 | 2-methylthiazol-4-yl-CH2-C(O)NH-CH2-COOCH3 | NH | H | H |
| 16 | 2-methylthiazol-4-yl-CH2-C(O)NH-CH2-COOC2H5 | NH | H | H |
| 17 | 2-methylthiazol-4-yl-CH2-C(O)NH-CH(CH(CH3)2)-CO2CH3 | NH | H | H |
| 18 | 2-methylthiazol-4-yl-CH2-C(O)NH-CH(CH(CH3)2)-CO2C2H5 | NH | H | H |
| 18a | 2-methylthiazol-4-yl-CH2-C(O)NH-CH(CH(CH3)2)-COOt-Bu | NH | H | H |

-continued
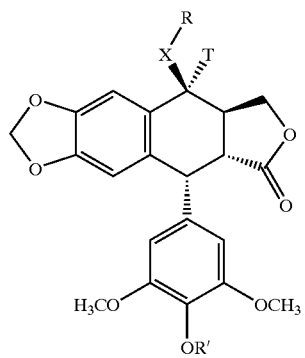
| Compound ID | R | X | T | R' |
|---|---|---|---|---|
| 19 | 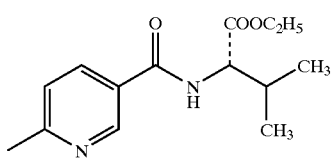 | NH | H | H |
| 20 | 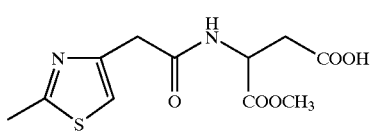 | NH | H | H |
| 21 | 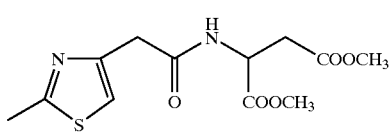 | NH | H | H |
| 22 | 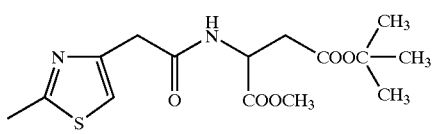 | NH | H | H |
| 23 | 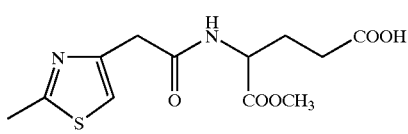 | NH | H | H |
| 24 | 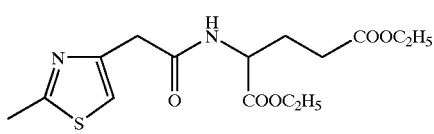 | NH | H | H |
| 25 | 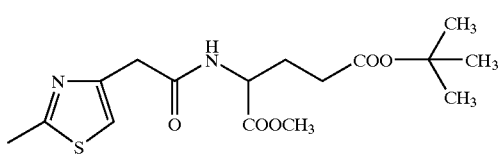 | NH | H | H |

-continued

| Compound ID | R | X | T | R' |
|---|---|---|---|---|
| 26 | ethyl 2-[[2-(2-methylthiazol-4-yl)acetyl]amino]-3-(1H-imidazol-4-yl)propanoate | NH | H | H |
| 27 | N-[3-(1H-imidazol-1-yl)propyl]-2-(2-methylthiazol-4-yl)acetamide | NH | H | H |
| 28 | 2-(2-methylthiazol-4-yl)-N-[3-(morpholin-4-yl)propyl]acetamide | NH | H | H |
| 29 | methyl N²-[2-(2-methylthiazol-4-yl)acetyl]-N⁶-(tert-butoxycarbonyl)lysinate | NH | H | H |
| 29a | methyl N²-[2-(2-methylthiazol-4-yl)acetyl]lysinate | NH | H | H |
| 30 | ethyl 2-[[(2-methyl-4,6-dioxo-1,4,5,6-tetrahydropyridin-3-yl)carbonyl]amino]-3-phenylpropanoate | NH | H | H |
| 31 | ethyl 2-[[2-(2-methylthiazol-4-yl)acetyl]amino]-3-(benzylthio)propanoate | NH | H | H |

-continued
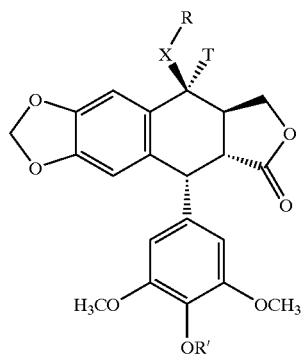
| Compound ID | R | X | T | R' |
|---|---|---|---|---|
| 32 | (2-methylthiazol-4-yl)CH₂C(O)NH-CH(Ph)-CO₂C₂H₅ | NH | H | H |
| 33 | (2-methylthiazol-4-yl)CH₂C(O)NH-CH(CH₂Ph)-C(O)NH-CH₂COOCH₃ | NH | H | H |
| 34 | (2-methylthiazol-4-yl)CH₂C(O)NH-O-Si(Ph)₂(t-Bu) | NH | H | H |
| 35 | (2-methylthiazol-4-yl)CH₂C(O)NH-OH | NH | H | H |
| 36 | (2-methylthiazol-4-yl)CH₂C(O)OCH₃ | NH | H | H |
| 37 | (6-methylpyridin-3-yl)C(O)OCH₃ | NH | H | H |
| 38 | (2-methylthiazol-4-yl)CH₂COOCH₂CH₃ | NH | H | H |

-continued
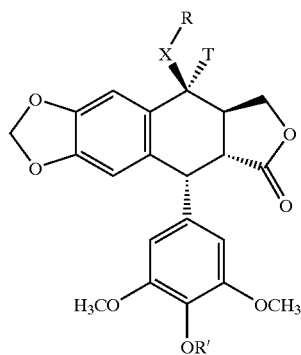
| Compound ID | R | X | T | R' |
|---|---|---|---|---|
| 39 | ![6-methylpyridin-3-yl ethyl ester] | NH | H | H |
| 40 | ![2-methylthiazol-4-yl acetic acid butyl ester] | NH | H | H |
| 41 | ![2-methylthiazol-4-yl acetic acid benzyl ester] | NH | H | H |
| 42 | ![2-methylthiazol-4-yl acetic acid 4-nitrobenzyl ester] | NH | H | H |
| 43 | 2,4-dimethylthiazole | NH | H | H |
| 44 | 2-methylthiazole | NH | H | H |
| 45 | 3,5-dimethylisothiazole | NH | H | H |
| 46 | 2,4,5-trimethylthiazole | NH | H | H |

-continued
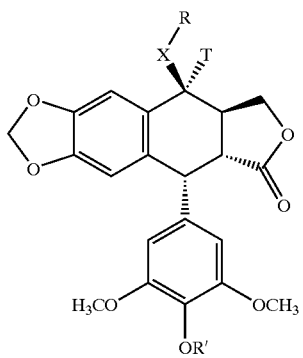
| Compound ID | R | X | T | R' |
|---|---|---|---|---|
| 47 | ethyl 2,4-dimethylthiazole-5-carboxylate | NH | H | H |
| 48 | 2-methyl-5-(4-nitrophenylsulfonyl)thiazole | NH | H | H |
| 49 | 2-methyl-5-nitrothiazole | NH | H | H |
| 50 | 2-methyl-5-nitropyridine | NH | H | H |
| 51 | 5-chloro-2-methylpyridine | NH | H | H |
| 52 | 4-(4-chlorophenyl)-2-methylthiazole | NH | H | H |
| 53 | 2-methyl-4-(4-methylphenyl)thiazole | NH | H | H |

-continued
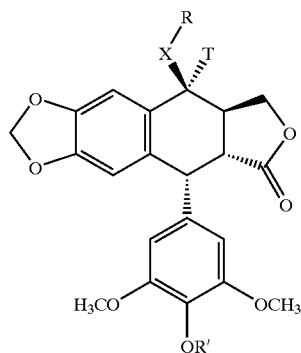
| Compound ID | R | X | T | R' |
|---|---|---|---|---|
| 54 | 2-(4-phenylthiazolyl) | NH | H | H |
| 55 | 2-methyl-5-thiazolyl (with CH3) | NH | H | H |
| 56 | 2-methyl-4-tert-butylthiazolyl | NH | H | H |
| 57 | 5-methyl-2-(methylthio)-1,3,4-thiadiazolyl | NH | H | H |
| 58 | 5-methyl-2-(ethylthio)-1,3,4-thiadiazolyl | NH | H | H |
| 59 | 5-methyl-2-ethyl-1,3,4-thiadiazolyl | NH | H | H |
| 60 | 2,5-dimethyl-1,3,4-thiadiazolyl | NH | H | H |
| 61 | 5-methyl-1,3,4-thiadiazolyl | NH | H | H |
| 62 | 5-methyl-2-amino-1,3,4-thiadiazolyl | S | H | H |
| 63 | 5-methyl-2-mercapto-1,3,4-thiadiazolyl | NH | H | H |

-continued
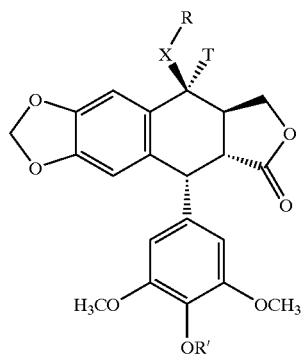
| Compound ID | R | X | T | R' |
|---|---|---|---|---|
| 64 | 5-methyl-3-phenyl-1,2,4-thiadiazole | NH | H | H |
| 65 | 3-methyl-1H-pyrazole | NH | H | H |
| 66 | 5-methyl-3-(methylthio)-4H-1,2,4-triazole | NH | H | H |
| 67 | 3-methyl-1H-pyrazole-4-carboxylic acid | NH | H | H |
| 68 | 3-methyl-1H-pyrazole-4-carbonitrile | NH | H | H |
| 69 | ethyl 5-methyl-1-phenyl-1H-pyrazole-4-carboxylate | NH | H | H |
| 70 | 5-methyl-3-mercapto-1,2,4-triazole | NH | H | H |

-continued

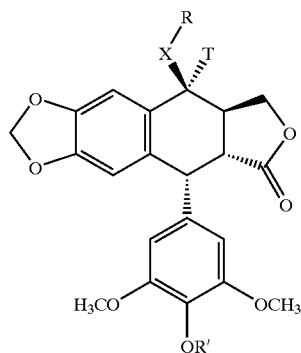

| Compound ID | R | X | T | R' |
|---|---|---|---|---|
| 71 | 3-amino-5-methyl-1H-1,2,4-triazole | S | H | H |
| 72 | 3,5-dibromo-2-methylpyridine | NH | H | H |
| 73 | 5-methyl-1H-tetrazole | NH | H | H |
| 74 | 4-methylpyrimidine | NH | H | H |
| 75 | 2-chloro-4-methylpyridine | NH | H | H |
| 76 | 3,5-dichloro-2-methylpyridine | NH | H | H |
| 77 | 2-(dimethylamino)ethyl 4-methyl-1H-pyrrole-3-carboxylate | NH | H | H |
| 78 | 2-(dimethylamino)ethyl 2-(2-methylthiazol-4-yl)acetate | NH | H | H |
| 79 | 2-(dimethylamino)ethyl 6-methylpyridine-3-carboxylate | NH | H | H |

-continued

| Compound ID | R | X | T | R' |
|---|---|---|---|---|
| 80 | 2-methylthiazol-4-yl-CH₂-C(O)-NH-CH₂CH₂-N(CH₃)₂ | NH | H | H |
| 81 | 3-methyl-1H-pyrazol-4-yl-C(O)-NH-CH₂CH₂-N(CH₃)₂ | NH | H | H |
| 82 | 6-methylpyridin-3-yl-C(O)-NH-CH₂CH₂-N(CH₃)₂ | NH | H | H |
| 83 | 1,2-dimethyl-1H-benzimidazol-? | NH | H | H |
| 84 | ethyl 3-methyl-1H-pyrazole-4-carboxylate | NH | H | H |
| 85 | ethyl 1,5-dimethyl-1H-pyrazole-4-carboxylate | NH | H | H |
| 86 | 6-methylpyrazin-2-yl | NH | H | H |

-continued
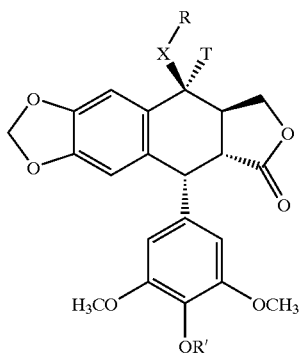
| Compound ID | R | X | T | R' |
|---|---|---|---|---|
| 87 | 3-methyl-5-hydroxy-1H-pyrazole | NH | H | H |
| 88 | 3-amino-5-methyl-1H-pyrazole | O | H | H |
| 89 | 5-methyl-1H-imidazole-4-carboxamide | NH | H | H |
| 90 | 1-methyl-1H-benzotriazole | O | H | H |
| 91 | 3-methyl-1H-1,2,4-triazole | NH | H | H |
| 92 | 3,5-dimethylisoxazole | | =N | H |
| 93 | 2,4-dimethylquinoline | NH | H | H |
| 94 | 3-methylquinoline | NH | H | H |

-continued
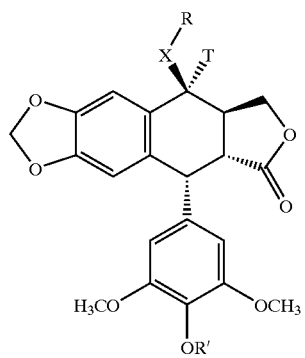
| Compound ID | R | X | T | R' |
|---|---|---|---|---|
| 95 | 8-methylquinoline | NH | H | H |
| 96 | benzyl 6-methylnicotinate | NH | H | H |
| 97 | 6-chloro-2-methylbenzothiazole | NH | H | H |
| 98 | 3,5-dimethylisoxazole | NH | H | H |
| 99 | 2-cyclopropyl-5-methyl-1,3,4-thiadiazole | NH | H | H |
| 100 | 4-methyl-5-nitro-2-methylpyridine | NH | H | H |
| 101 | 2-methoxy-4-methylpyridine | NH | H | H |
| 102 | (2-methylthiazol-4-yl)methanol | NH | H | H |

-continued
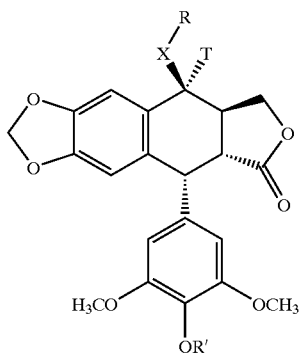
| Compound ID | R | X | T | R' |
|---|---|---|---|---|
| 103 | 2-methyl-6-methoxybenzothiazole | NH | H | H |
| 104 | 2-methyl-5-fluoropyridine | NH | H | H |
| 105 | 2-methyl-6-methylbenzothiazole | NH | H | H |
| 106 | 3-methyl-5-nitrobenzisothiazole | NH | H | H |
| 107 | 5-methyl-2-(N,N-diethylamino)pyridine | NH | H | H |
| 108 | 2-methyl-4-methoxybenzothiazole | NH | H | H |
| 109 | 3-methyl-4-bromo-5-phenylpyrazoline | NH | H | H |
| 110 | 2-methyl-5-(trifluoromethyl)-1,3,4-thiadiazole | NH | H | H |
| 111 | 5-methyl-2-bromopyridine | NH | H | H |

-continued
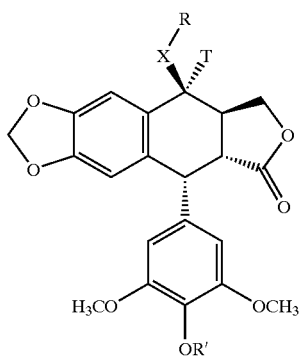
| Compound ID | R | X | T | R' |
|---|---|---|---|---|
| 112 | 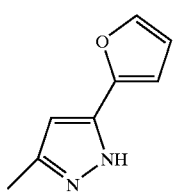 | NH | H | H |
| 113 | 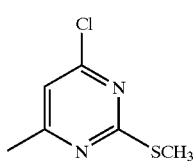 | NH | H | H |
| 114 | 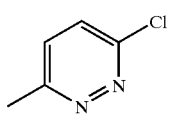 | NH | H | H |
| 115 | 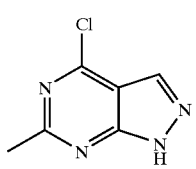 | NH | H | H |
| 116 | 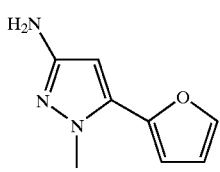 | NH | H | H |
| 117 | 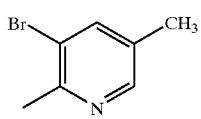 | NH | H | H |
| 118 | 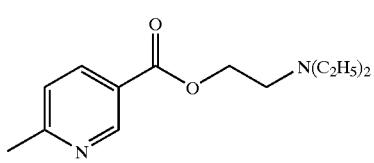 | NH | H | H |

-continued

| Compound ID | R | X | T | R' |
|---|---|---|---|---|
| 119 | 4-methyl-6-methoxypyrimidine | NH | H | H |
| 120 | 2-methyl-6-fluorobenzothiazole | NH | H | H |
| 121 | 2-methyl-6-chlorobenzoxazole | NH | H | H |
| 122 | 2-methyl-6-nitrobenzothiazole | NH | H | H |
| 123 | 3-hydroxy-2-methylpyridine | NH | H | H |
| 124 | 3,5,6-trimethyl-1,2,4-triazine | NH | H | H |
| 125 | 4-chloro-2-methyl-6-methoxypyrimidine | NH | H | H |
| 126 | 6-methyl-N-methoxynicotinamide | NH | H | H |
| 127 | 2-methoxy-5-methylpyridine | NH | H | H |

-continued

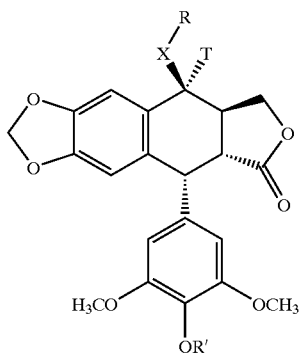

| Compound ID | R | X | T | R' |
|---|---|---|---|---|
| 128 | 3-methyl-1H-pyrazole-4-carboxylic acid 2-(dimethylamino)ethyl ester | NH | H | H |
| 129 | 6-ethoxy-2-methylbenzothiazole | NH | H | H |
| 130 | N-(3-methylisothiazol-5-yl)-2-(2-methylthiazol-4-yl)acetamide | NH | H | H |
| 131 | N-(2-chloropyridin-4-yl)-2-(2-methylthiazol-4-yl)acetamide | NH | H | H |
| 132 | 5-tert-butyl-3-methylisoxazole | NH | H | H |
| 133 | 3-(benzyloxy)-2-methylpyridine | NH | H | H |
| 134 | 2,4-dimethylpyridine | NH | H | H |
| 135 | (6-methylpyridin-3-yl)methanol | NH | H | H |

-continued
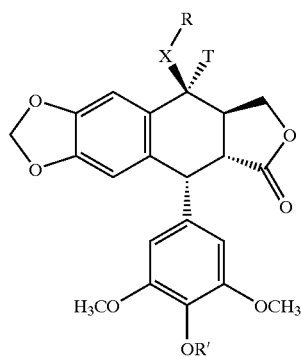
| Compound ID | R | X | T | R' |
|---|---|---|---|---|
| 136 | 5,6-dimethylbenzothiazol-2-yl (2-methyl) | NH | H | H |
| 137 | 6-methylpyridin-2-yl | NH | H | H |
| 138 | benzothiazol-2-yl | NH | H | H |
| 139 | 4-methylbenzothiazol-2-yl | NH | H | H |
| 140 | N-(2-chloropyridin-4-yl)-6-methylnicotinamide | NH | H | H |
| 141 | 6-ethoxy-3-methylpyridin-... | NH | H | H |
| 142 | 2-ethoxy-3-methylpyridin-... | NH | H | H |
| 143 | 5-iodo-6-methylpyridin-2-yl | NH | H | H |

-continued

| Compound ID | R | X | T | R' |
|---|---|---|---|---|
| 144 | 4-methyl-2,1,3-benzothiadiazole | NH | H | H |
| 145 | 2-[(2-methylthiazol-4-yl)]-N-[4-({[(5-nitropyridin-2-yl)amino]carbonyl}methyl)thiazol-2-yl]acetamide | NH | H | H |
| 146 | 2-(2-methylthiazol-4-yl)-N-(4-methyloxazol-2-yl)acetamide | NH | H | H |
| 147 | 4-methyl-2-mercaptopyrimidine | NH | H | H |
| 148 | 5-methyl-2-morpholinopyridine | NH | H | H |
| 149 | 5-methyl-1H-indole | NH | H | H |
| 150 | 4-(4-methoxyphenyl)-2-methylthiazole | NH | H | H |

-continued

| Compound ID | R | X | T | R' |
|---|---|---|---|---|
| 151 | 4,5-dimethyl-3-methylisoxazole (H3C, CH3, CH3 on isoxazole) | NH | H | H |
| 152 | 2-ethyl-benzothiazole | NH | H | H |
| 153 | 2-methyl-6-amino-benzimidazole | S | H | H |
| 154 | 2-methyl-6-(SCHF2)-benzothiazole | NH | H | H |
| 155 | 2-methyl-5-chloro-benzoxazole | NH | H | H |
| 156 | 6-methyl-benzothiazole | NH | H | H |
| 157 | 5-methyl-2-mercapto-benzimidazole | NH | H | H |
| 158 | 2-methyl-6-(SO2CH3)-benzothiazole | NH | H | H |
| 159 | 4-bromo-3,5-dimethyl-isothiazole | NH | H | H |

-continued
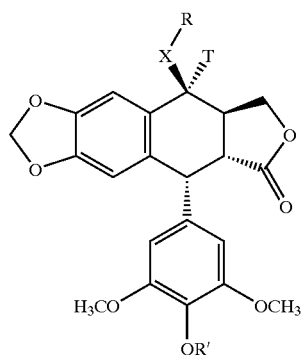
| Compound ID | R | X | T | R' |
|---|---|---|---|---|
| 160 | 2-methyl-5-nitropyridin-yl | O | H | H |
| 161 | 2,6-dimethyl-1H-indol-yl | NH | H | H |
| 162 | 6-chloro-3-methylpyridin-yl | — | H | H |
| 163 | 6-methyl-N-(4-nitrophenyl)nicotinamide | NH | H | H |
| 164 | 4-bromo-3,5-dimethylisoxazol-yl | NH | H | H |
| 165 | 2-(2-methylthiazol-4-yl)-N-(4-nitrophenyl)acetamide | NH | H | H |
| 166 | 2-methylthiazolo[5,4-c]pyridin-yl | S | H | H |
| 167 | 4-chloro-2-methylbenzothiazol-yl | NH | H | H |

-continued
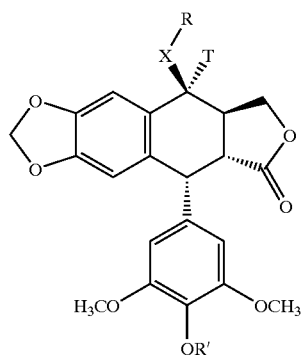
| Compound ID | R | X | T | R' |
|---|---|---|---|---|
| 168 | 6-bromo-2-methylbenzothiazole | NH | H | H |
| 169 | 2-chloro-3-methylpyridine | NH | H | H |
| 170 | 3,4,5-trimethylisoxazole | NH | H | H |
| 171 | 2,5-dimethylpyridine | O | H | H |
| 172 | 4-(4-trifluoromethylphenyl)-3,5-dimethylisoxazole | NH | H | H |
| 173 | 5-bromo-2-(5-methylisothiazol-3-yl)thiophene | NH | H | H |
| 174 | 4-cyano-3,5-dimethylisoxazole | NH | H | H |

-continued
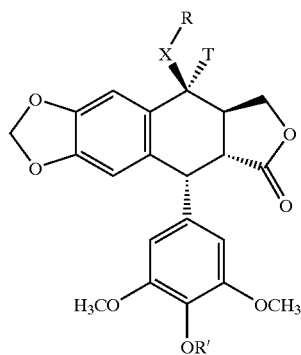
| Compound ID | R | X | T | R' |
|---|---|---|---|---|
| 175 | 2-methylbenzimidazole | NH | H | H |
| 176 | 1-methyl-3-(thiophen-2-yl)-pyrazole | — | H | H |
| 177 | 4-bromo-3-methyl-1-methyl-pyrazole | — | H | H |
| 178 | 2-methyl-4-oxo-thiazoline | NH | H | H |
| 179 | N-acetyl-3,4-dimethyl-isothiazol-5-yl | NH | H | H |
| 180 | 4,5,6-trifluoro-2-methyl-benzothiazole | NH | H | H |
| 181 | 4-methoxy-6-nitro-2-methyl-benzothiazole | NH | H | H |

-continued
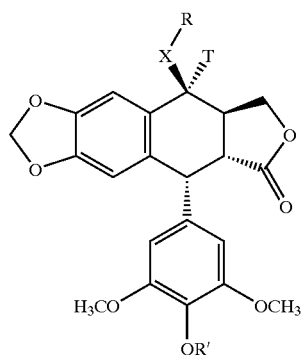
| Compound ID | R | X | T | R' |
|---|---|---|---|---|
| 182 | (2-methyl-[1,3]dioxino-fused benzothiazole) | NH | H | H |
| 183 | (4,6-difluoro-2-methylbenzothiazole) | NH | H | H |
| 184 | (6-methyl-1H-indazole) | NH | H | H |
| 185 | (6-acetamido-2-methylbenzothiazole) | NH | H | H |
| 186 | (2-(5-methylthiophen-3-yl)benzofuran) | NH | H | H |
| 187 | (6-ethoxy-2-methylbenzothiazole) | NH | H | H |
| 188 | (6-methyl-2-mercaptobenzothiazole) | NH | H | H |
| 189 | (4-nitro-3,5-dimethylisothiazole) | NH | H | H |

-continued
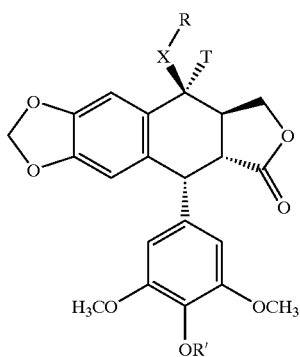
| Compound ID | R | X | T | R' |
|---|---|---|---|---|
| 190 | ClH₂C-C(O)-NH-(4,3-dimethylisothiazol-5-yl) | NH | H | H |
| 191 | H₃COH₂C-C(O)-NH-(4,3-dimethylisothiazol-5-yl) | NH | H | H |
| 192 | 5-methyl-1H-indazol-yl | NH | H | H |
| 193 | 4-bromo-3-methyl-5-phenyl-4,5-dihydro-1H-pyrazol-yl | NH | H | H |
| 194 | 4,7-dimethyl-2-oxo-naphthalen-yl | NH | H | H |
| 195 | 1-methyl-5-methyl-3-phenyl-pyrazol-yl | NH | H | H |
| 196 | 6-methyl-3H-isobenzofuran-1-on-yl | NH | H | H |

-continued
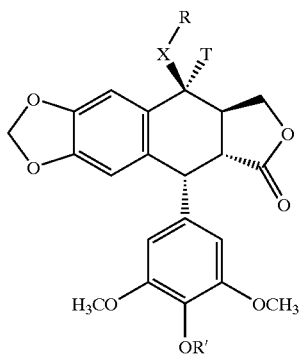
| Compound ID | R | X | T | R' |
|---|---|---|---|---|
| 197 | (6-methyl-3-oxo-4-(methoxymethyl)-3,4-dihydronaphthalen-1-yl) | NH | H | H |
| 198 | 2-methyl-4-methyl-3-carbamoylthiophene | NH | H | H |
| 199 | 5-methyl-3-thioxo-3H-1,2,4-dithiazole | NH | H | H |
| 200 | 2-methyl-4-(diethylaminomethyl)thiazole | NH | H | H |
| 201 | 2-methyl-4-(hydroxymethyl)thiazole | NH | H | H |
| 202 | 2-methyl-4-phenyl-5-tridecylthiazole | NH | H | H |
| 203 | 1,5-dimethyl-2-phenyl-4-methyl-3-imino-pyrazole | NH | H | H |

-continued

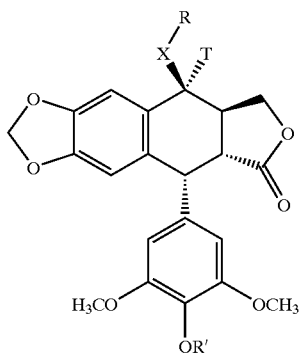

| Compound ID | R | X | T | R' |
|---|---|---|---|---|
| 204 | (5-methyl-isoindole-1,3-dione) | NH | H | H |
| 205 | (3-methyl-2-thioxo-thiazolidin-4-one) | NH | H | H |
| 206 | (2,6-dimethyl-benzothiazole) | NH | H | H |
| 207 | (3,5-dimethyl-isothiazole) | NH | H | $OPO_3H_2$ |
| 208 | (3,5-dimethyl-isoxazole) | NH | H | $OPO_3H_2$ |
| 209 | (2-methyl-thiazole) | NH | H | $OPO_3H_2$ |
| 210 | (2-methyl-thiazole-5-ethyl-$OPO_3H_2$) | NH | H | $OPO_3H_2$ |

The podophyllotoxin derivatives described above include the compounds themselves, as well as their salts and their prodrugs, if applicable. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, tartrate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the podophyllotoxin derivatives described above.

In addition, the just-described podophyllotoxin derivatives may have one or more double bonds, or one or more additional asymmetric centers. Such compounds can occur as racemates, racemic mixtures, single enantiomers, individual diastereomers, and diastereomeric mixtures.

Another aspect of the present invention relates to a pharmaceutical composition that contains a pharmaceutically acceptable carrier and an effective amount of at least one of the podophyllotoxin derivatives described above.

A further aspect of this invention relates to a method for treating cancer, e.g., carcinoma or sarcoma. The method includes administering to a subject in need thereof an effective amount of one or more the aforementioned podophyllotoxin derivatives.

As used herein, "cancer" refers to a cellular tumor. Cancer cells have the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate cancer, colorectal cancer, cancer of the head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site. In addition, cancer can be associated with a drug resistance phenotype.

Also within the scope of this invention is a composition containing one or more of the podophyllotoxin derivatives described above for use in treating cancer, and the use of such a composition for the manufacture of a medicament for cancer treatment.

Other features or advantages of the present invention will be apparent from the following detailed description of several embodiments, and also from the appending claims.

DETAILED DESCRIPTION

The podophyllotoxin derivatives described above can be prepared by methods well known in the art, as well as by the synthetic routes disclosed herein. See, e.g., Wang et al. (1992) *Yaoxue Xuebao* 27: 656; Lee et al. (1989) *J. Nat. Prod.* 52: 606; and Chen et al. (2000) *Chinese Chemical Letters* 11: 505. For example, as shown in the scheme below, one can use podophyllotoxin as a starting material. Bromination of podophyllotoxin gives an intermediate, 4'-O-demethyl-4β-bromo-4-desoxypodophylotoxin (Kuhn, et al. (1969) *Helv. Chim. Acta* 52: 944). The intermediate reacts with an amino substituted heteroaryl or heterocyclyl side chain in the presence of a weak base, e.g., barium carbonate, to provide a podophyllotoxin derivative of this invention as shown in the scheme below (Y in the scheme is as defined in Summary). The amino substituted heteroaryl or heterocyclyl moiety is synthesized by a cyclization reaction followed by modifications on its substituents.

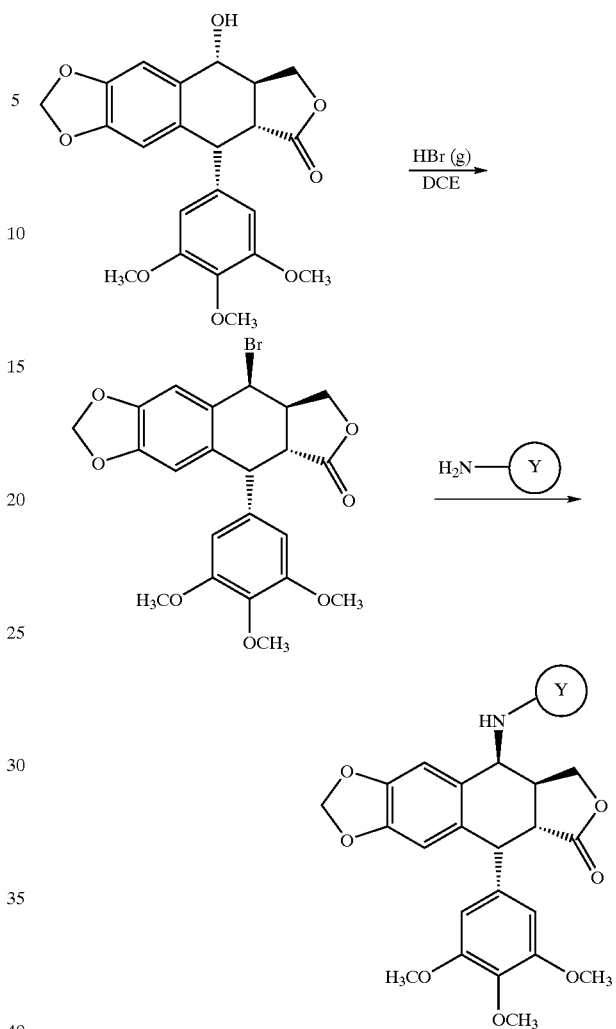

Alternatively, a compound of this invention can be synthesized by coupling of the aforementioned intermediate with a mercapto or hydroxyl substituted heteroaryl.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the podophyllotoxin derivative. In addition, various synthetic steps may be performed in an alternate sequence or order to give the desired compounds. Synthetic chemistry transformations and protecting group methodologies (protection and deprotection) useful in synthesizing applicable podophyllotoxin derivatives are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A podophyllotoxin derivative thus synthesized can be further purified by a method such as column chromatography, High-Performance Liquid Chromatography (HPLC), High-Performance Flash Chromatography (HPFC), or recrystallization.

Podophyllotoxin derivative phosphate prodrugs of this invention are further prepared according to the method described in U.S. Pat. No. 4,904,768 and U.S. Pat. No. 5,606,039. They are synthesized by reacting podophyllotoxin derivatives with phosphorous oxychloride in an appropriate solvent, e.g., acetonitrile, in the presence of an organic base, e.g., N,N-diisopropylethtylamine.

This invention features a method for treating cancer. The method includes administering to a subject in need thereof an effective amount of one or more podophyllotoxin derivatives described in Summary and a pharmaceutically acceptable carrier. The term "treating" is defined as the application or administration of a composition including the podophyllotoxin derivative to a subject, who has cancer, a symptom of cancer, or a predisposition toward cancer, with the purpose to cure, heal, alleviate, relieve, alter, remedy, ameliorate, improve, or affect cancer, the symptoms of cancer, or the predisposition toward cancer. "An effective amount" is defined as the amount of a podophyllotoxin compound which, upon administration to a subject in need thereof, is required to confer therapeutic effect on the subject. An effective amount of a podophyllotoxin derivative may range from about 0.2 mg/Kg to about 60 mg/Kg. Effective doses also vary, as recognized by those skilled in the art, depending on route of administration, excipient usage, and the possibility of co-usage with other therapeutic treatments such as use of other anticancer agents or radiation therapy. Examples of the other anticancer agents include paclitaxel, docitaxel, doxorubicin, daunorubicin, epirubicin, fluorouracil, melphalan, cis-platin, carboplatin, cyclophosphamide, mitomycin C, methotrexate, mitoxantrone, vinblastine, vincristine, ifosfamide, teniposide, etoposide, bleomycin, leucovorin, cytarabine, dactinomycin, interferon alpha, streptozocin, prednisolone, procarbazine, irinotecan, topotecan, colony stimulating factor, granulocyte/monocyte colony stimulating factor, and imatinib mesylate.

To practice the method of the present invention, a podophyllotoxin derivative can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with podophyllotoxin derivatives), can be utilized as pharmaceutical excipients for delivery of podophyllotoxin derivatives. Examples of other carriers include colloidal silicon dioxide, magnesium stearate, cellulose, sodium lauryl sulfate, and D&C Yellow #10.

Podophyllotoxin derivatives of this invention can be preliminarily screened for their efficacy in treating cancer by in vitro assays. For example, podophyllotoxin derivatives can be tested for their cytotoxicity against KB cells (nasopharyngeal carcinoma). More specifically, a test compound can be added to a culture of KB cells and its $IC_{50}$ (i.e., the concentration of the test compound which achieves a half-maximal inhibition of cell growth) is determined using the sulforhodamine B (a protein binding dye) assay as described in *J.N.C.I.* (1990) 82: 1107. The podophyllotoxin derivatives of this invention are also tested for their abilitives to inhibit DNA topoisomerase II in vitro as described in Cho et al. (1996 *J. Med. Chem.* 39: 1396) and to stimulate protein-linked DNA breaks (PLDB) in KB cells as described in Rowe et al. (1986 *Cancer Res.* 46:2021). DNA topoisomerase II is a well known target for cancer treatment drugs. See, e.g., MacDonald et al. (1991) *DNA Topoisomerase in Cancer*; Oxford University Press: New York.

Podophyllotoxin derivatives of this invention can further be screened for their efficacy in treating caner by in vivo assays. For example, a test compound can be injected into an animal (e.g., a mouse model) and its therapeutic effects are then accessed. Based on the results, an appropriate dosage range and administration route can also be determined.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

Chemical Syntheses

As used herein, melting points were determined on a Fisher-John melting point apparatus and are uncorrected. Proton Nuclear Magnetic Resonance ($^1$H NMR) spectra were measured on a Varian 300 or a Bruker 400 (if indicated) spectrometer with tetramethylsilane (TMS) as the internal standard. Chemical shifts are reported in δ (ppm). Mass spectra (MS) were obtained on an API 3000 LC/MS/MS spectrometer. Flash column chromatography was performed on silica gel (100–200 mesh). HPFC was conducted on a Biotage Horizon system. Precoated silica gel plates (Kieselgel 60 $F_{254}$, 0.25 mm) were used for thin layer chromatography (TLC) analysis.

Synthesis of Compounds 1–2, 7–9, 12–13, 15–18, 20–26, 29, 29a, 31, and 32

These compounds were synthesized starting from podophyllotoxin as shown in Scheme 1 below. Bromination of podophyllotoxin gave an intermediate, 4'-O-demethyl-4β-bromo-4-desoxypodophylotoxin (referred to as DBD hereinafter). Hydrolyzing the methyl ester in Compound 7 with 2N HCl in THF afforded Compound 9. Removal of the tert-butyl and Boc groups in Compounds 22, 25 and 29 with trifluoroacetic acid (TFA), in the presence of anisole, gave Compounds 20, 23 and 29a, respectively. More specifically, 4β-N-linked -(substituted heteroaryl)-4'-O-demethyl 4-epipodophyllotoxin was synthesized as follows. To a solution of DBD in an appropriate solvent mixture (e.g., THF and 1,2-dichloroethane (DCE) (1:1)/or acetonitrile (1:1)) was added an amino substituted heteroaryl (1.2 equivalent) and $BaCO_3$ (1.5 equivalents). The mixture was heated to reflux under nitrogen with TLC or LC-MS monitoring. The reaction mixture was cooled to room temperature and a solid was formed and filtered. The filtrate thus obtained was concentrated to provide a crude product. The crude product was purified by silica gel column chromatography with $CH_2Cl_2$:EtOAc:acetone, EtOAc:hexanes:MeOH, or $CH_2Cl_2$:MeOH as the eluant.

Analytical data on two compounds are shown below.

Compound 2, i.e., 4'-O-demethyl-4β-[4"-(ethyl L-tryptophan-N-acetyl)-2"-thiazolyl amino]-4-desoxypodophyllotoxin. ESI MS: 754 [M+H], 753 [M−H]; $^1$H NMR (300 MHz, $CDCl_3$) δ: 8.35 (br s, 1H, NH), 7.96 (d, J=8 Hz, 1H, 7'''-H), 7.42 (d, J=8 Hz, 1H, 4'''-H), 7.05 (s, 1H, 3'''-H), 6.97 (m, 2H, 5''', 6'''-H), 6.82 (s, 1H, H-5), 6.49 (s, 1H, 8-H), 6.30 (s, 2H, 2', 6'-H), 6.22 (s, 1H, 5''-H), 5.95 (2H, d, J=12 Hz, $OCH_2O$), 4.98 (m, 2H, 4, 9'''-H), 4.51 (d, J=5 Hz, 1H, 1-H), 4.12 (t, J=7 Hz, 2H, $OCH_2CH_3$), 3.82 (s, 6H, 3', 5'-$OCH_3$), 3.52 (d, J=7 Hz, 2H, 6''-H), 3.42 (m, 2H, 11, 8'''-H), 3.28 (dd, J=4, 15 Hz, 1H, 8'''-H), 3.16 (t, J=10 Hz, 1H, 11-H), 2.78 (dd, J=5, 14 Hz, 1H, 2-H), 2.58 (m, 1H, 3H).

Compound 32, i.e., 4'-O-demethyl-4β-[4"-(ethyl L-phenylglycyl-N-acetyl)-2"-thiazolyl amino]-4-desoxypodophyllotoxin. Amorphous, mp 150–153° C. (dec.); ESI MS: 700.4 [M−H]; $^1$H NMR (300 MHz, $CDCl_3$): δ 8.21 (br. d, J=7.1 Hz, 1H, NH of amino acid), 7.35–7.23 (m, 5H, Benzene ring of amino acid), 6.90 (s, 1H, 5-H), 6.52 (s, 1H, 8-H), 6.32 (s, 2H, 2'-H, 6'-H), 6.29 (s, 1H, S—C$\underline{H}$—), 5.96 (d, 2H, J=11.0 Hz, —$OCH_2O$—), 5.54 (d, J=7.1 H, 1H, CONH—C$\underline{H}$), 5.32 (br. s, 1H, 4-H), 4.57 (d, J=4.4 Hz, 1H, 1-H), 4.25 (dd, J=6.6, 8.8 Hz, 1H, 11β-H), 4.14 (q, J=7.1 Hz, 2H, $CH_2CH_3$), 3.92 (t, J=9.6 Hz, 1H, 11α-H), 3.77 (s, 6H, 3',5'-$OCH_3$), 3.52 (s, 2H, $CH_2$CONH), 2.98 (m, 2H, 2-H, 3-H), 1.26, 1.18 (total 3H, both t, J=7.1 Hz, $CH_2\underline{CH_3}$, isomer ratio=2:5).

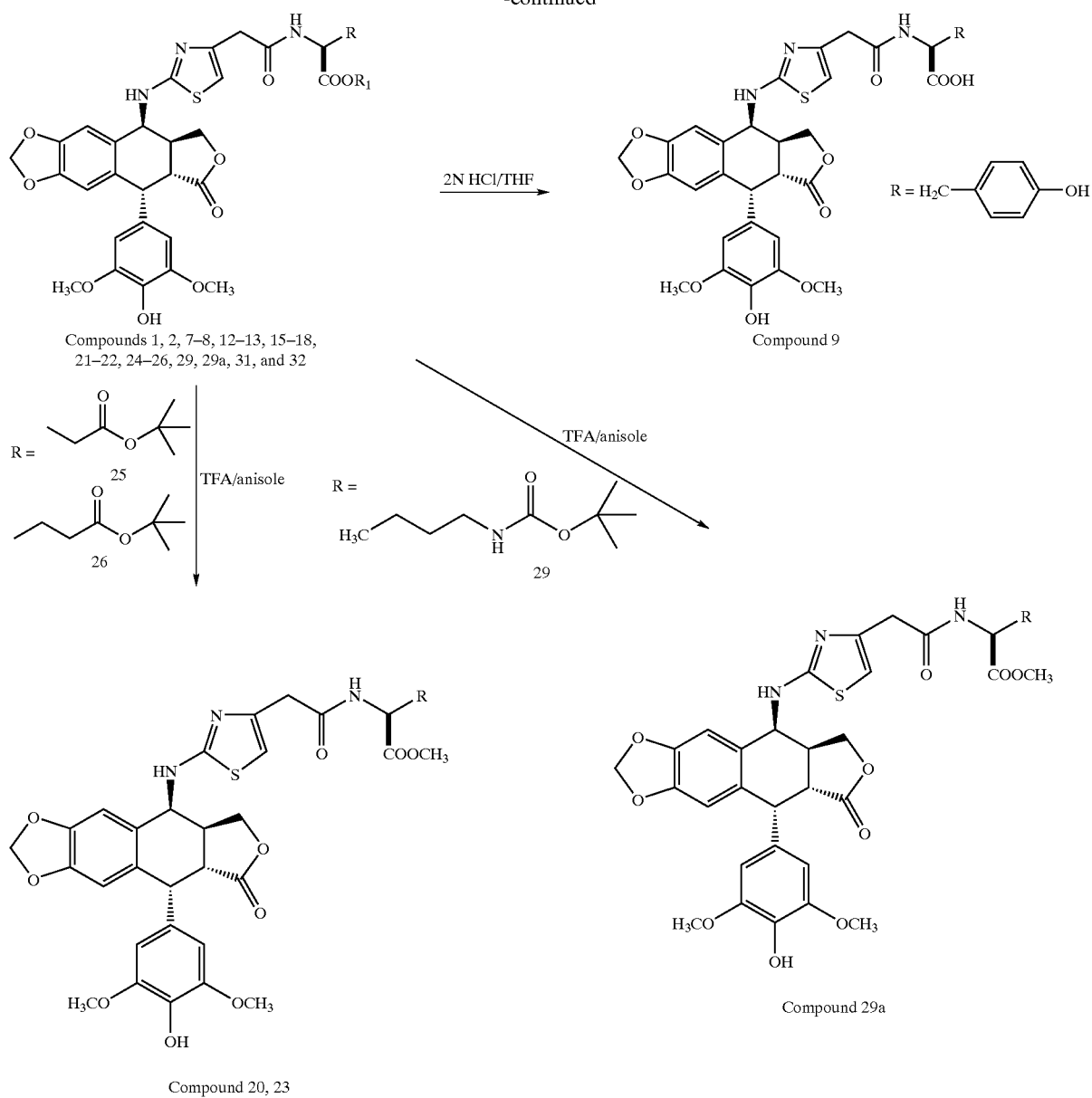

Synthesis of Compounds 6, 11, 36–42, 77–82, 96, 118, 126, 128, 130, 131, 140, 145, 146, 163, and 165

Each of Compounds 36 and 37 was synthesized as follows. Reaction of an amino substituted heteroaryl with (trimethylsilyl) diazomethane (2.0 M solution in hexanes) in a solvent of methanol and benzene yielded an intermediate. Substitution of the intermediate at C-4 position of DBD gave the desired product. See Scheme 2 below.

Analytical data on Compound 36 are shown below.

Compound 36, i.e., 4'-O-demethyl-4β-[4"-(methyl-O-acetyl)-2"-thiazolylamino]-4-desoxypodophyllotoxin. Yield 59%; Amorphous, mp 116–120° C. (dec.); ESI MS: 553 [M−H], 577 [M+Na]. $^1$H NMR (CDCl$_3$) δ 6.85 (s, 1H, 5-H), 6.52 (s, 1H, 8-H), 6.38 (s, 1H, 5"-H), 6.30 (s, 2H, 2',6'-H), 5.98 and 5.96 (dd, 2H, —OCH$_2$O—), 5.16 (br, 1H, 4-H), 4.59 (br, 1H, 1-H), 4.40 (t, 1H, 11-H), 3.95 (t, 1H, 11-H), 3.79 (s, 6H, 3',5'-OCH$_3$), 3.73 (s, 3H, —COOCH$_3$), 3.60 (s, 2H, —CH$_2$COOCH$_3$), 3.00 (m, 2H, 2-H, 2-H).

Compounds 6, 11, 38–42, 77–82, 84, 96, 118, 126, 128, 130–131, 140, 145–146, 163, and 165 were synthesized by coupling an appropriate alcohol or amine to an amino substituted heteroaryl followed by conjugation with DBD.

Analytical data on a number of compounds are shown below.

Compound 39, i.e., 4'-O-demethyl-4β-[5"-(ethoxycarbonyl)-2"-pyridylamino)]-4-desoxypodophyllotoxin. Yield 35%; Amorphous, mp 164–168° C. (dec.); ESI MS: 547 [M−H], 571[M+Na]. $^1$H NMR (CDCl$_3$) δ 8.78 (d, 1H, J=2.2 Hz, 6"-H), 8.04 and 8.01(dd, J=2.2 Hz, 1H, 4"-H), 6.79 (s, 1H, 5-H), 6.55 (s, 1H, 8-H), 6.42 (d, J=8.8 Hz, 1H, 5"-H), 6.33 (s, 2H, 2',6'-H), 5.99, 5.96 (dd, J=1.6 Hz, 2H, —OCH$_2$O—), 5.46 (br, 2H, 4-H, NH), 4.88 (d, J=5.5 Hz, 1H, 1-H), 4.62 (br, 1H, 11-H), 4.40 (br, 1H, 11-H), 4.36 (q, J=7.1 Hz, 2H, CH$_2$CH$_3$), 3.79 (s, 6H, 3',5'-OCH$_3$), 3.03 (m, 2H, 2-H, 2-H), 1.36 (t, J=7.1 Hz, 3H, CH$_2$CH$_3$).

Compound 84, i.e., 4'-O-demethyl-4β-[4"-(ethoxycarbonyl)-3"-pyrazolylamino]-4-desoxypodophyllotoxin. Yield 40%; White solid, mp 152–155° C. (dec.); ESI MS: 536 [M−H]. $^1$H NMR (CDCl$_3$) δ 7.32 (s, 1H, 5"-H), 6.66 (s, 1H, 5-H), 6.62 (s, 1H, 8-H), 6.31 (s, 2H, 2',6'-H), 6.01, 6.00 (dd, J=1.1 Hz, 2H, —OCH$_2$O—), 5.45 (s, 1H, NH), 5.43 (d, J=4.9 Hz, 1H, 4-H), 4.70 (d, J=4.9 Hz, 1H, 1-H), 4.68 (br, 1H, 11-H), 4.36 (br, 1H, 11-H), 4.25 (m, 2H, CH$_2$CH$_3$), 3.79 (s, 6H, 3',5'-OCH$_3$), 3.55 (m, 1H, 3-H,), 3.25 (dd, J=4.9 Hz, 1H, 2-H,), 1.35 (t, J=7.1 Hz, 3H, CH$_2$CH$_3$).

Compound 140, i.e., 4'-O-demethyl-4β-[2"-(3'"-(2'"-chloro-4'"-pyridinylamino-carbonyl))-pyridinlylamino]-4-desoxypodophyllotoxin. Amorphous, mp >240° C. (dec); ESI MS: 630.0 (M−1); $^1$H NMR δ (400 MHz, CDCl$_3$): 8.65 (1H, d, J=2.3 Hz, 3'"-H of second pyridine), 8.32 (1H, d, J=5.5 Hz, 6'"-H of second pyridine), 7.95 (1H, dd, J=2.3, 9.0 Hz, 4"-H of first pyridine), 7.76 (1H, d, J=2.0 Hz, 6"-H of first pyridine), 7.48 (1H, dd, J=2.0, 5.9 Hz, 5'"-H of second pyridine), 6.79 (1H, s, 5-H), 6.56 (1H, s, 8-H), 6.50 (1H, d, J=9.0 Hz, 3"-H of first pyridine), 6.34 (2H, s, 2'-H, 6'-H), 5.98 (2H, d d, J=1.2, 6.7 Hz, —OCH$_2$O—), 5.44 (1H, d. J=5.5 Hz, 4-H), 4.63 (1H, d, J=3.9 Hz, 1-H), 4.42 (1H, dd, J=7.0, 9.4 Hz, 11α-H), 3.80 (1H, d, J=2.2, 8.8 Hz, 2-H), 3.80 (6H, s, 3',5'-OCH$_3$), 3.50 (1H, m, 3-H), 3.03 (1H, br. d, J=4.7 Hz, 11β-H).

Scheme 2

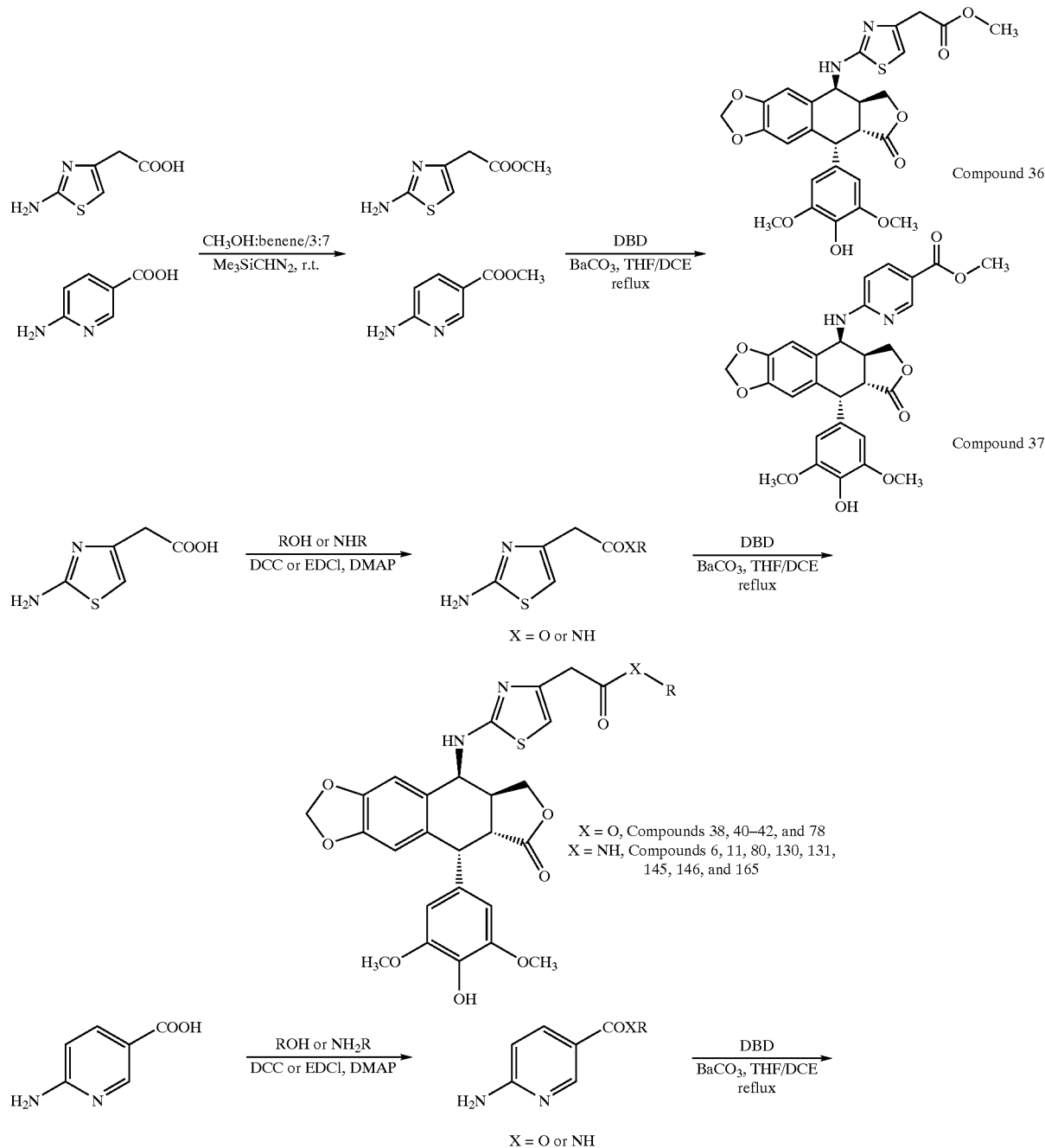

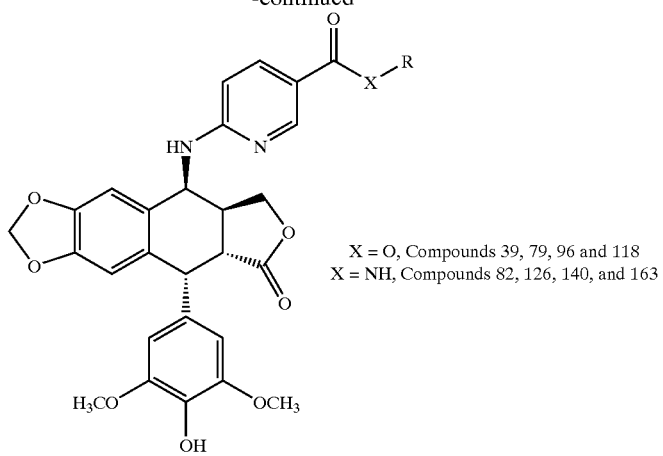

X = O, Compounds 39, 79, 96 and 118
X = NH, Compounds 82, 126, 140, and 163

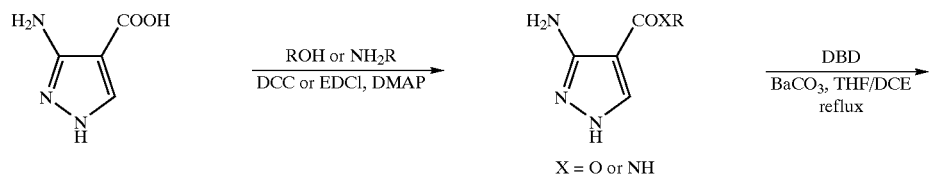

X = O or NH

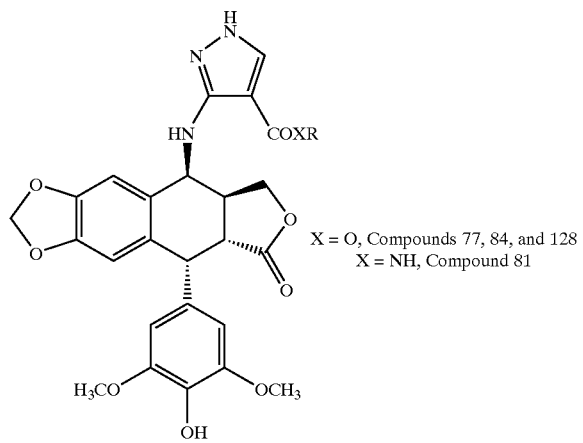

X = O, Compounds 77, 84, and 128
X = NH, Compound 81

Synthesis of Compound 3–5, 10, 14, 19, and 30

These compounds were synthesized as shown in Scheme 3. Analytical data on Compound 14 are shown below.

Compound 14, i.e., 4'-O-demethyl-4β-[4"-(ethyl L-phenylglycyl-N-acetyl)-2"-thiazolyl amino]-4-desoxypodophyllotoxin. Amorphous, mp 233–236° C. (dec.); ESI MS: 694.4 [M−1]; $^1$H NMR (300 MHz, CDCl$_3$): δ 8.48 (d, J=3.3 Hz, 1H, 6"-H), 7.77 (dd, J=2.7, 8.8 Hz, 1H, 4"-H), 7.34–7.21 (m, 3H, 3'"-H, 4'"-H, 5'"-H), 7.17 (dd, J=1.6, 6,6 Hz, 2H, 2'"-H, 6'"-H), 6.78 (s, 1H, 5-H), 6.52 (s, 1H, 8-H), 6.46 (d, J=8.8 Hz, 1H, 3"-H), 6.32 (s, 2H, 2'-H, 6'-H), 5.95 (dd, J=1.6, 6.6 Hz, 2H, —OCH$_2$O—), 5.00 (t, J=6.3 Hz, 1H, 4-H), 4.58 (d, J=4.9 Hz, 1H, 1-H), 4.41 (br.d, J=7.1 Hz, 1H, 11β-H), 4.21 (q, J=7.4 Hz, 2H, —C$\underline{H}_2$CH$_3$), 3.83 (dd-like, 1H, 11α-H), 3.77 (s, 6H, 3',5'-OCH$_3$), 3.22 (m, 2H, 2-H, 3-H), 3.20 (m, 2H, C$\underline{H}_2$ of benzyl), 1.27 (t, J=7.1 Hz, 3H, —CH$_2$C$\underline{H}_3$).

Scheme 3

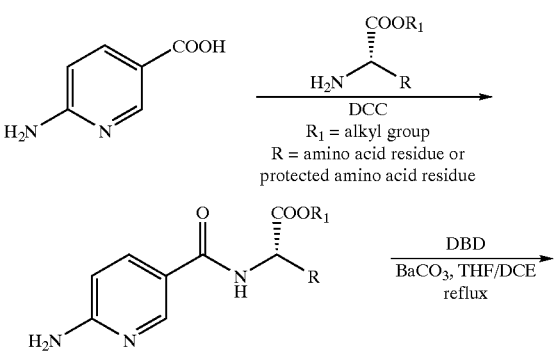

$R_1$ = alkyl group
R = amino acid residue or protected amino acid residue

71

-continued

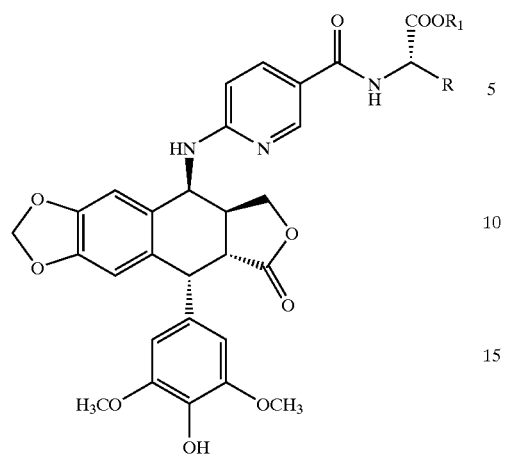

Compounds 3, 10, 14, and 19

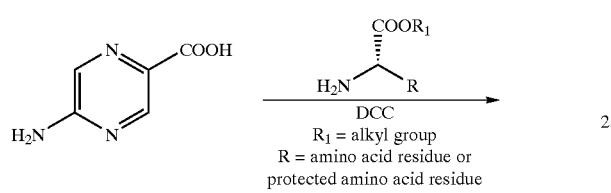

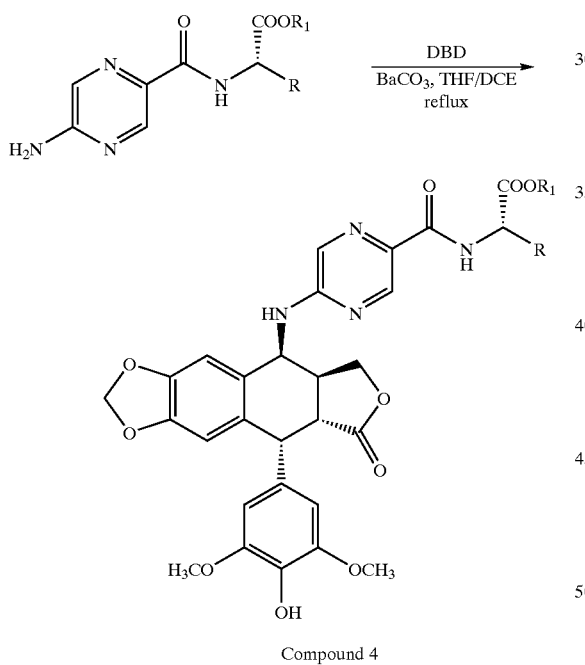

Compound 4

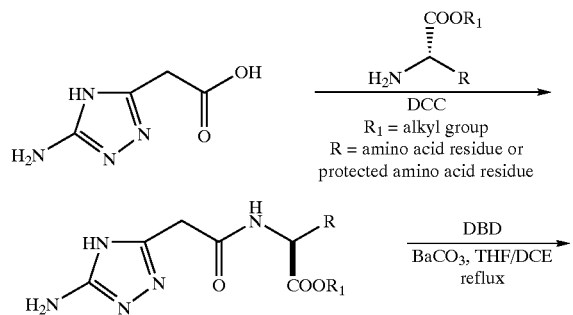

72

-continued

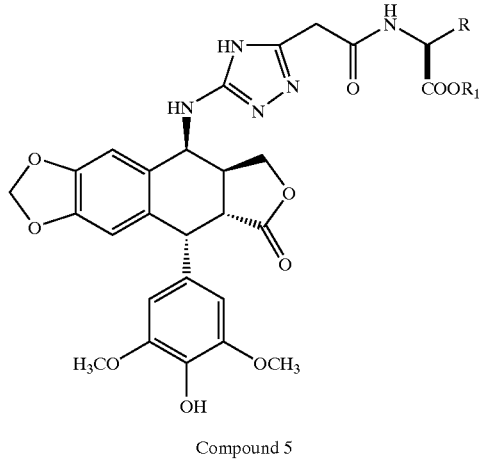

Compound 5

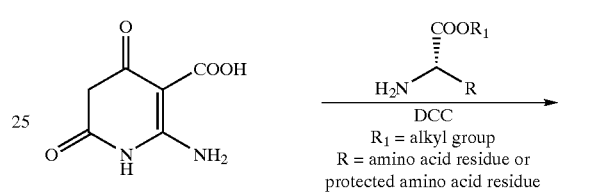

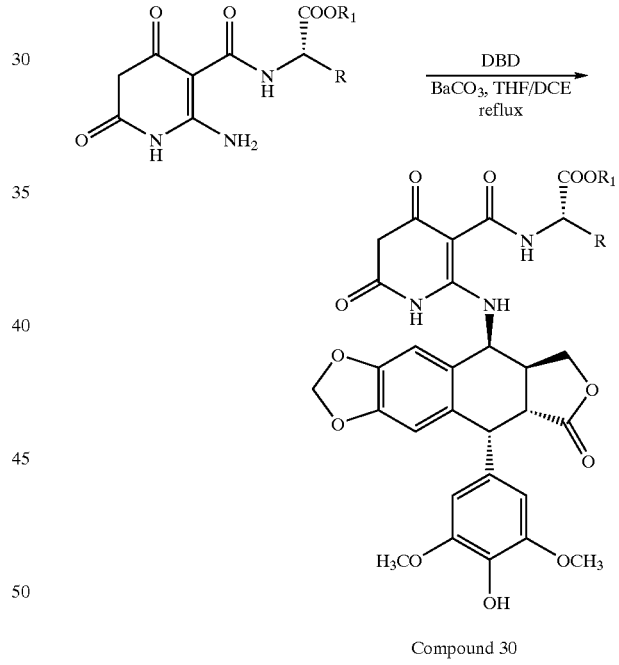

Compound 30

Synthesis of Compounds 27, 28, and 33–35

Compounds 27 and 28 were synthesized as shown in Scheme 4. Reaction of 1-(3-aminopropyl)-imidazole or 4-(3-aminopropyl)-morpholine with an amino substituted heteroaryl in the presence of isobutyl chloroformate and N-methyl morpholine afforded an amide compound. The amide compounds further reacted with DBD to give the desire product.

Analytical data on Compound 28 are shown below.

Compound 28: 4'-O-demethyl-4β-[4"-(4'"-(3'"-aminopropyl)-morpholine-N-acetyl)-2"-thiazolylamino]-4-desoxypodophyllotoxin. Amorphous, mp 105–109° C. (dec.); ESI MS: 667 [M+H]. $^1$H NMR (CDCl$_3$) δ 6.84 (s, 1H, 5-H), 6.54 (s, 1H, 8-H), 6.35 (s, 1H, 5"-H), 6.31 (s, 2H, 2',6'-H), 6.00 (m, 2H, —OCH$_2$O—), 5.08 (m, 1H, 4-H), 4.60

(d, J=2.7 Hz, 1H, 1-H), 4.25 (m, 2H, C$\underline{H_2}$CH$_3$), 4.38 (m, 1H, 11-H), 3.88 (m, 1H, 11-H), 3.79 (s, 6$\underline{H}$, 3',5'-OCH$_3$), 3.66 (t, 4H, 2''',6'''-CH$_2$— on morpholine ring), 3.47 (s, 2$\underline{H}$, CH$_2$CO on thiazole), 3.33 (m, 2H, CONHCH$_2$CH$_2$C$\underline{H_2}$—), 3.02 (br, 2H, 2-H, 3-H,), 2.38 (m, 6H, 3''',5'''-CH$_2$— on morpholine ring and CONHCH$_2$CH$_2$C$\underline{H_2}$—), 1.70 (m, 2H, CONHCH$_2$C$\underline{H_2}$CH$_2$—).

Compound 33 was synthesized from a dipeptide as shown in Scheme 4. Methylation of the dipeptide under refluxing in acetyl chloride and methanol produced a methyl ester. Reaction of the methyl ester with an amino substituted heteroaryl gave an amine compound as a white crystal. The amine compound further react with DBD to give the desired product.

Compounds 34 and 35 were synthesized by coupling of tert-butyl diphenylsilyl protected hydroxylamine to an amino substituted heteroaryl followed by conjugation with DBD (Scheme 4). Compounds 34 and 35 were obtained by silica gel column chromatography.

Analytical data on these two compounds are shown below.

Compound 34, i.e., 4'-O-demethyl-4β-[4''-(O-tert-butyl diphenylsilylhydroxyl)-N-acetyl) -2''-thiazolylamino]-4-desoxypodophyllotoxin. Amorphous, mp 155–158° C. (dec.); ESI MS: 792 [M−H]. $^1$H NMR (CDCl$_3$) δ 9.10 (br, 1H, NH), 7.72 (m, 4H, 2''', 6'''-H— on O-tert-butyl diphenylsilylhydroxyl), 7.34 (m, 6H, 3''', 4''', 5'''-H— on O-tert-butyl diphenylsilylhydroxyl), 6.68 (s, 1H, 5-H), 6.56 (s, 1H, 8-H), 6.32 (s, 2H, 2',6'-H), 6.17 (s, 1H, 5''-H), 6.00 (m, 2H, —OCH$_2$O—), 5.97 (m, 1H, 4-H), 4.70 (br, 1H, 11-H), 4.61 (d, J=4.9 Hz, 1H, 1-H), 4.08 (br, 1H, NH), 3.88 (br, 1H, 11-H), 3.80 (s, 6H, 3',5'-OC$\underline{H_3}$), 3.35 (s, 2H, C$\underline{H_2}$CO on thiazole), 3.02 (m, 1H, 3-H), 2.90 (m, 1H, 2-H), 1.11 (s, 9H, CH$_3$ on t-butyl).

Compound 35, i.e., 4'-O-demethyl-4β-[4''-(O-hydroxylamine)-N-acetyl)-2''-thiazolylamino]-4-desoxypodophyllotoxin. Amorphous, mp 165–168° C. (softened), 210–213 (dec.); ESI MS m/e: 555 [M+H], 577 [M+Na]. $^1$H NMR (CDCl$_3$) δ 6.63 (s, 1H, 5-H), 6.52 (s, 1H, 8-H), 6.34 (s, 1H, 5''-H), 6.31 (s, 2H, 2', 3'-H), 5.97 (d, J=6.0 Hz, 2H, —OCH$_2$O—), 4.90 (d, J=4.4 Hz, 1H, 4-H), 4.60 (d, J=4.4 Hz, 1H, 1-H), 4.35 (m, 1H, 11-H), 3.84–3.90 (br, 1H, 11-H), 3.79 (s, 6H, 3', 5'-OC$\underline{H_3}$), 3.44 (s, 2H, C$\underline{H_2}$CO on thiazole), 3.25 (dd, J=5.5 Hz, 1H, 2-H), 3.00 (m, 1H, 3-H).

Scheme 4

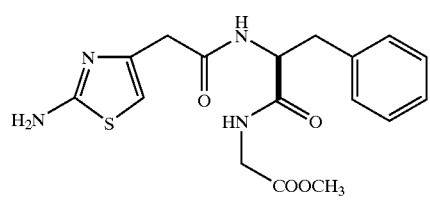

-continued

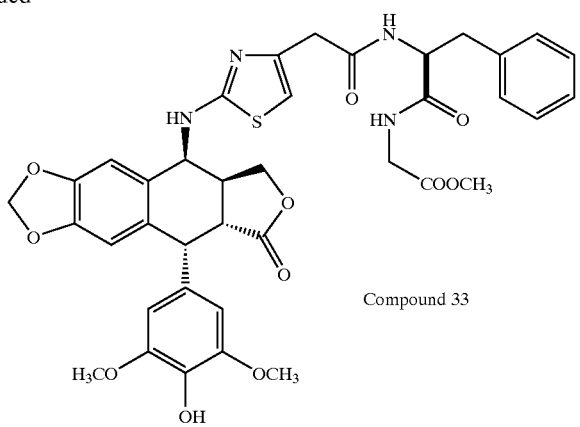

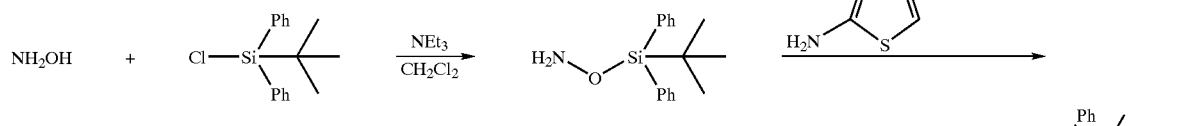

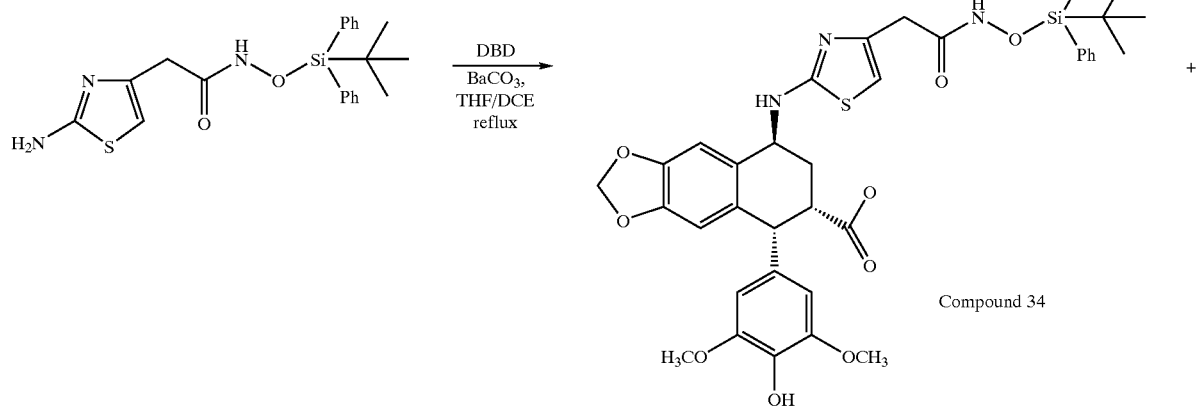

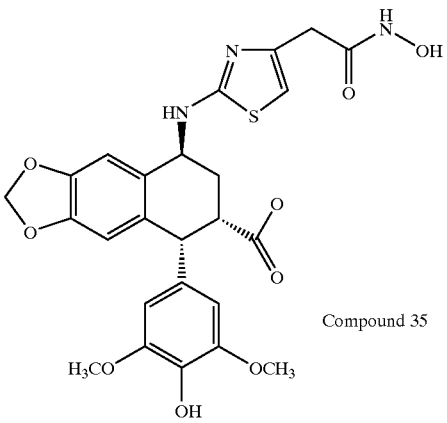

Synthesis of Compounds 43–76, 85–90, 97–101, 103–106, 108–117, 119–125, 127, 129, 132–134, 136–139, 143–144, 147, 149–158, 160–162, 164, 166–178, 180–188, 192–199, and 202–206

These compounds were synthesized by reacting an amino or a hydroxyl substituted heteroaryl with DBD in the presence of barium carbonate.

Analytical data on a number of compounds are shown below.

Compound 45, i.e., 4'-O-demethyl-4β-(5"-ethoxycarbonyl-4"-methyl-2"-thiazolyl amino)-4-desoxypodophyllotoxin. Amorphous, mp 257–259° C. (dec.); ESI MS: 495.2 (M−H); $^1$H NMR(300 MHz, CDCl$_3$+ CD$_3$OD): δ 7.37 (s, 1H, 4-H of thiazole), 6.83 (s, 1H, 5-H), 6.53 (s, 1H, 8-H), 6.31 (s, 2H, 2'-H, 6'-H), 6.01 (br. d, J=14.3 Hz, 2H, —OCH$_2$O—), 5.97 (s, 1H, OH), 4.59 (d, J=4.9 Hz, 1H, 4-H), 4.47 (d, J=4.4 Hz, 1H, 1-H), 4.39 (t, J=8.8 Hz, 1H, 11β-H), 4.02 (t, J=7.1 Hz, 1H, 3-H), 3.78 (s, 6H, 3',5'-

OCH₃), 3.13 (dd-like, J=4.9, 13.7 Hz, 1H, 11α-H), 3.03 (m, 1H, 2-H), 2.31 (s, 3H, —CH₃).

Compound 47, i.e., 4'-O-demethyl-4β-(5"-ethoxycarbonyl-4"-methyl-2"-thiazolyl amino)-4-desoxypodophyllotoxin. ESI MS: 567.3 [M–H]; (300 MHz, CDCl₃) δ: 6.82 (s, 1H, 5-H), 6.53 (s, 1H, 8-H), 6.30 (s, 2H, 2', 6'-H), 5.98 (d, J=7 Hz, 2H, OCH₂O), 5.39 (m, 1H, NH), 5.13 (d, J=4 Hz, 4-H), 4.59 (d, J=4 Hz, 1H, 1-H), 4.43 (t, J=8 Hz, 1H, 11-H), 4.28 (q, J=7 Hz, 2H, OC$\underline{H}_2$CH₃), 3.92 (m, 1H, 11-H), 3.78 (s, 6H, 3', 5'-OCH₃), 2.98 (m, 2H, 2, 3-H), 2.55 (s, 3H, 4"-CH₃), 1.34 (t, J=7 Hz, 3H, OCH₂C$\underline{H}_3$).

Compound 49, i.e., 4'-O-demethyl-4β-(5"-nitro-2"-thiazolyl amino)-4-desoxypodophyllotoxin. Amorphous, mp 201–203° C. (dec.); ESI MS: 526.3 (M–H); ¹H NMR (300 MHz, CDCl₃): δ 8.05 (s, 1H, —H of thiazole), 6.81 (s, 1H, 5-H), 6.56 (s, 1H, 8-H), 6.29 (s, 2H, 2'-H, 6'-H), 5.99 (br. s, 2H, —OCH₂O—), 5.28 (br. s, 1H, 4-H), 4.61 (d, J=5.0 Hz, 1H, 1-H), 4.44 (br. d, J=7.4, 8.8 Hz, 1H, 11β-H), 3.89 (t, J=9.8 Hz, 1H, 11α-H), 3.78 (s, 6H, 3',5'-OCH₃), 3.04 (m, 1H, 2-H), 2.95 (dd, J=4.7, 14.0 Hz, 1H, 3-H).

Compound 50, i.e., 4'-O-demethyl-4β-(5"-nitro-2"-pyridylamino)-4-desoxypodophyllotoxin. Yellow crystals, mp >250° C. (dec.); ESI MS: 520.3 (M–H); ¹H NMR (300 MHz, CDCl₃+CD₃OD): δ 9.03 (br. s, 1H, 6"-H), 8.16 (d, J=9.3 Hz, 1H, 4"-H), 6.80 (d, J=3.3 Hz, 1H, 5-H), 6.56 (dd, J=3.3, 8.8 Hz, 1H, 4"-H), 6.55 (d, J=3.3 Hz, 1H, 8-H), 6.35 (s, 2H, 2'-H, 6'-H), 5.98 (br. t, J=4.1 Hz, 2H, —OCH₂O—), 5.62 (br. s, 1H, 4-H), 4.64 (d, J=3.8 Hz, 1H, 1-H), 4.42 (br.dd, J=8.2, 1H, 14.8 Hz, 11β-H), 3.79 (s, 6H, 3',5'-OCH₃), 3.39 (d, J=3.8 Hz, 1H, 11α-H), 3.35 (m, 1H, 3-H), 3.15 (m, 1H, 2-H).

Compound 57, i.e., 4'-O-demethyl-4β-[5"-methylthio-2"-(1",3",4"-thiadiazolylamino)]-4-desoxypodophyllotoxin. Amorphous, mp 218–220° C. (dec.); ESI MS: 528.3 (M–H); ¹H NMR (300 MHz, CDCl₃+CD₃OD): δ 6.76 (s, 1H, 5-H), 6.55 (s, 1H, 8-H), 6.33 (s, 2H, 2'-H, 6'-H), 5.98 (br. d, J=2.2 Hz, 2H, —OCH₂O—), 5.84 (d. J=5.5 Hz, 1H, 4-H), 4.68 (d, J=4.9 Hz, 1H, 1-H), 4.44 (t, J=8.2 Hz, 1H, 11β-H), 3.80 (d, J=2.2, 8.8 Hz, 1H, 3-H), 3.78 (s, 6H, 3',5'-OCH₃), 3.67 (dd, J=4.6, 14.3 Hz, 1H, 11α-H), 3.12 (m, 1H, 2-H), 2.87 (s, 3H, SCH₃).

Compound 59, i.e., 4'-O-demethyl-4β-[5"-ethyl-2"-(1", 3",4"-thiadiazolylamino)]-4-desoxypodophyllotoxin. ESI MS: 510.2 (M–H); ¹H NMR (300 MHz, CDCl₃): δ 6.77 (s, 1H, 5-H), 6.56 (s, 1H, 8-H), 6.34 (s, 2H, 2', 6'-H), 5.97 (d, J=5 Hz, 2H, OCH₂O), 5.90(d, J=6 Hz, 1H, 4-H), 4.68 (d, J=5 Hz, 1H, 1-H), 4.42 (t, J=8 Hz, 1H, 11-H), 3.78 (s, 6H, 3', 5'-OCH₃), 3.68–3.83 (m, 2H, 2, 11-H), 3.09 (m, 1H, 3-H), 2.56 (q, J=7 Hz, 2, C$\underline{H}_2$CH₃), 1.15 (t, J=7 Hz, 3H, CH₂C$\underline{H}_3$).

Compound 66, i.e., 4'-O-demethyl-4β-[5"-methylthio-1"H-3"-(1",2",4"-triazolylamino)]-4-desoxypodophyllotoxin. Amorphous, mp 195–198° C. (dec.); ESI MS: 511.2 (M–H); ¹H NMR (300 MHz, CDCl₃+CD₃OD): δ 6.60 (d, J=4.4 Hz, 1H, NH of triazole), 6.61 (s, 1H, 5-H), 6.59 (s, 1H, 8-H), 6.34 (s, 2H, 2'-H, 6'-H), 5.97 (d, J=16.5 Hz, 2H, —OCH₂O—), 5.47 (br. s, 1H, NH on C-4), 5.39 (d, J=5.5 Hz, 1H, 4-H), 4.73 (d, J=4.9 Hz, 1H, 1-H), 4.44 (t, J=8.8 Hz, 1H, 11β-H), 4.27 (t, J=7.9 Hz, 1H, 3-H), 3.80 (s, 6H, 3',5'-OCH₃), 3.45 (dd, J=8.8, 10.4 Hz, 1H, 11α-H), 3.05 (m, 1H, 2-H), 2.72 (s, 3H, SCH₃).

Compound 72, i.e., 4'-O-demethyl-4β-(3",5"-dibromo-2"-pyridylamino)-4-desoxypodophyllotoxin. ESI MS: 633.3 (M–H); ¹H NMR (300 MHz, CDCl₃): δ 8.11 (d, J=2 Hz, 1H, 6"-H), 7.81 (d, J=2 Hz, 1H, 4"-H), 6.76 (s, 1H, 5-H), 6.56 (s, 1H, 8-H), 6.34 (s, 2H, 2', 6'-H), 5.99, 5.98 (each d, J=1 Hz, OCH₂O), 5.34 (d, 1H, NH), 5.11 (d, J=6 Hz, 1H, 4-H), 4.63 (d, J=4 Hz, 1H, 1-H), 4.37 (m, 1H, 11-H), 3.79 (s, 6H, 3', 5'-OCH₃), 3.71 (m, 1H, 11-H), 3.03 (m, 2H, 2, 3-H).

Compound 73, i.e., 4'-O-demethyl-4β-(1"H-5"-tetrazolylamino)-4-desoxypodophyllotoxin. Amorphous, mp 237–240° C. (dec.); ESI MS: 466.2 (M–H); ¹H NMR (300 MHz, CDCl₃+CD₃OD): δ 6.63 (s, 1H, 5-H), 6.60 (s, 1H, 8-H), 6.35 (s, 2H, 2'-H, 6'-H), 6.02 (s, 1H, NH of tetraazole), 5.97 (br. s, 2H, —OCH₂O—), 5.77 (d, J=5.5 Hz, 1H, 4-H), 4.77 (d, J=5.5 Hz, 1H, 1-H), 4.37 (t, J=7.9 Hz, 1H, 11β-H), 4.11 (t, J=7.1 Hz, 1H, 3-H), 3.78 (s, 6H, 3',5'-OCH₃), 3.68 (dd-like, J=4.9, 13.7 Hz, 1H, 11α-H), 3.30 (m, 1H, 2-H).

Compound 83, i.e., 4'-O-demethyl-4β-(1"-methyl-2"-benzimidazolylamino)-4-desoxypodophyllotoxin. White needles, mp 227–230° C. (dec.); ESI MS: 530 [M+H]. ¹H NMR (CDCl₃) δ 7.49, 7.18 (m, 1H each, H-4", 7"), 7.14 (m, 2H, H-5",6"), 6.89 (s, 1H, 5-H), 6.57 (s, 1H, 8-H), 6.32 (s, 2H, 2',6'-H), 6.00 (dd, J=1.1 Hz, 2H, —OCH₂O—), 5.52 (d, J=3.3, 1H, 4-H), 4.65 (d, J=4.4 Hz, 1H, 1-H), 4.51 (m, 1H, 11-H), 3.88 (m, 1H, 11-H), 3.79 (s, 6H, 3',5'-OC$\underline{H}_3$), 3.52 (s, 3H, NCH₃), 3.09 (m, 2H, 2-H, 3-H,).

Compound 85, i.e., 4'-O-demethyl-4β-[(1"-methyl-4"-ethoxycarbonyl)-5"-pyrazolylamino]-4-desoxypodophyllotoxin. Amorphous, mp 140–143° C. (dec.); ESI MS: 550.2 (M–H); ¹H NMR (300 MHz, CDCl₃+CD₃OD): δ 7.71 (s, 1H, 3"-H of pyrazole), 6.52 (s, 1H, 5-H), 6.50 (s, 1H, 8-H), 6.30 (s, 2H, 2'-H, 6'-H), 5.95 (dd, J=1.1, 7.1 2H, Hz, —OCH₂O—), 5.50 (s, 1H, 4'-OH), 4.92 (d, J=3.8 Hz, 1H, 4-H), 4.89 (d, J=3.8 Hz, 1H, 1-H), 4.64 (d, J=4.9 Hz, 1H, 3-H), 4.37 (dd, J=8.8, 15.9 Hz, 1H, 11-H), 4.18 (q, J=7.1 Hz, 2H, OCH₂CH3), 3.78 (s, 6H, 3',5'-OCH₃), 3.74 (s, 1H, N—CH₃), 3.16 (dd, J=4.9, 14.3 Hz, 1H, 11-H), 3.05 (m, 1H, 2-H), 1.27 (t, J=7.1 Hz, 3H, OCH2CH₃.

Compound 88, i.e., 4'-O-demethyl-4β-(3"-amino-5"-pyrazolyloxy)-4-desoxypodophyllotoxin. Amorphous, mp 250–253° C. (dec.); ESI MS: 480.1 (M–H); ¹H NMR (300 MHz, CDCl₃+CD₃OD): δ 6.85 (s, 1H, 5-H), 6.50 (s, 1H, 8-H), 6.30 (s, 2H, 2'-H, 6'-H), 5.96 (br. s, 2H, —OCH₂O—), 4.99 (br. s, 1H, 4-H), 4.56 (br. s, 1H, 1-H), 4.40 (br. d, 1H, J=8.8 Hz, 11β-H), 4.12 (m, 1H, 3-H), 3.97 (t, 1H, J=9.3 Hz, 11α-H), 3.75 (s, 6H, 3',5'-OCH₃), 3.05 (m, 1H, 2-H).

Compound 90, i.e., 4'-O-demethyl-4β-(1"-benzotriazolyloxy)-4-desoxypodophyllotoxin. ESI MS: 516.4 (M–H); ¹H NMR (300 MHz, CDCl₃): δ 8.07 (d, J=9 Hz, 7"-H), 7.56 (m, 2H, 5", 6"-H), 7.44 (s, 1H, 5-H), 6.63 (s, 1H, 8-H), 6.46 (s, 2H, 2', 6'-H), 6.07 (d, J=4 Hz, 2H, OCH₂O), 5.96 (d, J=9 Hz, 1H, 4"-H), 4.65 (d, J=2 Hz, 1H, 1-H, 3.82 (s, 6H, 3', 5'-OCH₃), 3.77 (m, 1H, 4-H), 3.69, 3.61 (each t, J=9 Hz, 11-H), 3.22 (m, 1H, 3-H), 2.88 (dd, J=15, 4 Hz, 1H, 2-H).

Compound 91, i.e., 4'-O-demethyl-4β-[3"-(1",2",4"-triazolylamino)-4-desoxypodophyllotoxin. Amorphous, mp 245–248° C. (dec.); ESI MS: 465.2 (M–H); ¹H NMR (300 MHz, CDCl₃+CD₃OD): δ 7.74 (br. s, 1H, NH of triazole), 7.38 (s, 1H, 5-H on triazole), 6.86 (s, 1H, 5-H), 6.53 (s, 1H, 8-H), 6.34 (s, 2H, 2'-H, 6'-H), 5.96 (d, J=3.3 Hz, 2H, —OCH₂O—), 5.03 (d, J=3.8 Hz, 1H, 4-H), 4.60 (d, J=4.9 Hz, 1H, 1-H), 4.43 (t, J=7.1 Hz, 1H, 11-H), 3.94 (t, J=9.1 Hz, 1H, 11-H), 3.79 (s, 6H, 3',5'-OCH₃), 3.19 (dd, J=49, 14.2 Hz, 1H, 3-H), 3.05 (m, 1H, 2-H).

Compound 94, i.e., 4'-O-demethyl-4β-(3"-quinolinylamino)-4-desoxypodophyllotoxin. ESI MS: 525.3 (M–H); ¹H NMR (300 MHz, CDCl₃): δ 8.43 (d, J=3 Hz, 1H, 2"-H), 7.96 (m, 1H, 8"-H), 7.63 (m, 1H, 5"-H), 7.47 (m, 2H, 6", 7"-H), 6.99 (d, J=3 Hz, 1H, 4"-H), 6.77 (s, 1H, 5-H), 6.54 (s, 1H, 8-H), 6.35 (s, 2H, 2', 6'-H), 5.96 (d, J=7 Hz, OCH₂O), 5.70 (br s, 1H, 4'-OH), 4.78 (m, 1H, NH), 4.60 (d, J=4 Hz, 1H, 4-H), 4.46 (d, J=6 Hz, 1H, 1-H), 4.44 (m, 1H, 11-H), 3.96 (t, J=9 Hz, 1H, 11-H), 3.79 (s, 6H, 3', 5'-OCH3), 3.14 (m, 2H, 2, 3-H).

Compound 98, i.e., 4'-O-demethyl-4β-[5"-(3"-methyl)-isoxazolylamino]-4-desoxypodophyllotoxin. Amorphous, mp 227–229° C. (dec.); ESI MS: 479.1 (M–H); $^1$H NMR δ (Bruker 400 MHz, CDCl$_3$): 6.80 (s, 1H, 5-H), 6.54 (s, 1H, 8-H), 6.30 (s, 2H, 2'-H, 6'-H), 5.98 (dd, 2H, J=1.2, 9.0 Hz, —OCH$_2$O—), 5.43 (s, 1H, 4"-H of isoxazole), 4.74 (d, J=3.5, 1H, 4-H), 4.60 (d, J=4.3 Hz, 1H, 1-H), 4.40 (dd, J=7.0, 8.2 Hz, 1H, 11β-H), 4.00 (t, J=9.0 Hz, 1H, 2-H), 3.79 (s, 6H, 3',5'-OCH$_3$), 3.03 (dd, J=4.7, 1H, 14.1 Hz, 11α-H), 2.98 (1H, m, 3-H), 2.20 (3H, s, CH$_3$ of isoxazole).

Compound 105, i.e., 4'-O-demethyl-4β-[2"-(5"-methyl)-benzothiazolylamino]-4-desoxypodophyllotoxin. Amorphous, mp 245–248° C. (dec.); ESI MS: 545.2 (M–1); $^1$H NMR δ (Bruker 400 MHz, CDCl$_3$): 7.45 (1H, d, J=8.2 Hz, 4"-H), 7.41 (1H, br. s, 7"-H), 7.15 (1H, br. d, J=8.2 Hz, 5"-H), 6.89, 6.54 (1H each, both s, 5-H, 8-H). 6.32 (2H, s, 2'-H, 6'-H), 5.98 (2H, dd, J=1.2, 7.8 Hz, —OCH$_2$O—), 5.42 (1H, d, J=3.9 Hz, 4-H), 4.61 (1H, d, J=4.3 Hz, 1-H), 4.50 (1H, dd, J=6.7, 9.0 Hz, 2-H), 3.98 (1H, dd, J=9.8, 20.0 Hz, 11α-H), 3.79 (6H, s, 3',5'-OCH$_3$), 3.08 (1H, m, 3-H), 3.01 (1H, dd, J=4.3, 13.7 Hz, 11β-H), 2.42 (3H, s, CH$_3$).

Compound 106, i.e., 4'-O-demethyl-4β-[3"-(5"-nitro)-benzisothiazolylamino]-4-desoxypodophyllotoxin. Amorphous, mp 114–117° C.; ESI MS: 576.3 (M–H); $^1$H NMR (Bruker 400 MHz, CDCl$_3$): δ 8.72 (s, 1H, 4"-H), 8.09 (dd, J=2.3, 12.1 Hz, 1H, 6"-H), 7.51 (d, J=9.8 Hz, 1H, 7"-H), 6.77 (s, 1H, 5-H), 6.62 (s, 1H, 8-H), 6.35 (s, 2H, 2', 6'-H), 5.99 (d, J=1.2 Hz, 2H, OCH$_2$O), 5.46 (br s, 1H, 4'-OH), 4.73 (d, J=4.7 Hz, 1H, 1-H), 4.46 (m, 1H, 4-H), 4.48 (t, J=7.0 Hz, 1H, 11-H), 3.95 (t, J=10.1 Hz, 1H, 11-H), 3.81 (s, 6H, 3', 5'-OCH3), 3.22 (m, 2H, 2, 3-H).

Compound 110, i.e., 4'-O-demethyl-4β-[2"-(5"-trifluroumethyl-1",3",4"-thiadiazolylamino)]-4-desoxypodophyllotoxin. Amorphous, mp 225–227° C. (dec.); ESI MS:550.4 (M–H); $^1$H NMR (Bruker 400 MHz, CDCl$_3$): δ 6.70 (1H, s, 5-H), 6.57 (1H, s, 8-H), 6.32 (2H, s, 2'-H, 6'-H), 6.00, (2H, dd, J=1.2, 4.3 Hz, —OCH$_2$O—), 5.97 (1H, d, J=5.5 Hz, 4-H), 4.71 (1H, d, J=4.7 Hz, 1-H), 4.42 (1H, dd, J=7.4, 8.8 Hz, 11β-H), 3.79 (6H, s, 3',5'-OCH$_3$), 3.70 (1H, dd, J=9.0, 11.0 Hz, 11α-H), 3.47 (1H, dd, J=4.7, 5.1 Hz, 2-H), 3.14 (1H, m, 3-H).

Compound 144, i.e., 4'-O-demethyl-4β-[4"-(2",1",3"-benzothiadiazolylamino)]-desoxypodophyllotoxin. Amorphous, mp 168–172° C.; ESI MS: 532.0 (M–H); $^1$H NMR (Bruker 400 MHz, CDCl$_3$): δ 7.48 (m, 1H, 6"-H), 7.36 (d, J=8.6 Hz, 1H, 7"-H), 6.77 (s, 1H, 5-H), 6.58 (s, 1H, 8-H), 6.36 (s, 2H, 2', 6'-H), 6.34 (d, J=7.8 Hz, 1H, 1H, 5"-H), 5.98 (dd, J=1.2, 8.6 Hz, 2H, OCH$_2$O), 5.43 (br s, 1H, 4'-OH), 4.88 (t, J=4.3 Hz, 1H, 4-H), 4.46 (d, J=4.7 Hz, 1H, 1-H), 4.44 (t, J=8.2 Hz, 1H, 11-H), 3.98 (t, J=10.6 Hz, 1H, 11-H), 3.81 (s, 6H, 3', 5'-OCH3), 3.24 (dd, J=4.7 Hz, 1H, 2-H), 3.13 (m, 1H, 3-H).

Compound 155, i.e., 4'-O-demethyl-4β-[2"-(5"-chlorobenzoxazolylamino)]-desoxypodophyllotoxin. Amorphous, mp 215–217° C. (dec.); ESI MS: 549.2 (M–H); $^1$H NMR (Bruker 400 MHz, CDCl$_3$): δ 6.95 (1H, d, J=8.2 Hz, 7"-H), 6.88 (1H, dd, J=2.0, 8.2 Hz, 6"-H), 6.72, 6.71 (1H each, both s, 5-H, 8-H). 6.37 (2H, s, 2'-H, 6'-H), 6.02 (2H, dd, J=1.2, 7.8 Hz, —OCH$_2$O—), 5.71 (1H, d, J=2.0 Hz, 4"-H), 5.67 (1H, d, J=5.1 Hz, 4-H), 4.81 (1H, d, J=5.1 Hz, 1-H), 4.58 (1H, dd, J=7.0, 9.4 Hz, 2-H), 3.87 (1H, dd, J=10.6, 18.8 Hz, 11α-H), 3.80 (6H, s, 3',5'-OCH$_3$), 3.18 (1H, m, 3-H), 3.01 (1H, dd, J=5.1, 14.5 Hz, 11β-H).

Compound 160, i.e., 4'-O-demethyl-4β-[2"-(5"-chloropyridinlyloxy)]-desoxypodophyllotoxin. Amorphous, mp 205–208° C. (dec); ESI MS: 521.2 (M–H); $^1$H NMR (Bruker 400 MHz, CDCl$_3$): δ 8.16 (1H, dd, J=3.1, 9.8 Hz, 4"-H of pyridine), 8.02 (1H, d, J=3.1 Hz, 6"-H of pyridine), 6.70 (1H, s, 5-H), 6.67 (1H, d, J=9.8 Hz, 3"-H of pyridine), 6.49 (1H, s, 8-H), 6.32 (2H, s, 2'-H, 6'-H), 6.24 (1H, d, J=5.1 Hz, 4-H), 6.06 (2H, br. dd, J=1.2, 2.3 Hz, —OCH$_2$O—), 4.79 (1H, d, J=5.1 Hz, 1-H), 4.48 (1H, dd, J=7.0, 9.4 Hz, 2-H), 3.81 (6H, s, 3',5'-OCH$_3$), 3.38 (1H, dd, J=9.4, 11.0 Hz, 11α-H), 3.28 (1H, m, 3-H), 2.75 (1H, dd, J=5.1 14.1 Hz, 11β-H).

Compound 188, i.e., 4'-O-demethyl-4β-[6"-(2"-mercaptobenzothiazolylamino)]-desoxypodophyllotoxin. Colorless needles, mp 219–221° C. (dec.); ESI MS: 563.4 (M–H); $^1$H NMR (Bruker 400 MHz, CDCl$_3$): δ 7.62 (1H, d, J=8.6 Hz, 4"-H of benzothiazole), 7.03 (1H, d, J=2.0 Hz, 7"-H of benzothiazole), 7.01 (1H, s, 5-H), 6.79 (1H, dd, J=2.0, 8.6 Hz, 5"-H of benzothiazole), 6.49 (1H, s, 8-H), 6.33 (2H, s, 2'-H, 6'-H), 5.97 (2H, dd, J=1.2, 9.4 Hz, —OCH$_2$O—), 5.66 (1H, d, J=3.9 Hz, 4-H), 4.60 (1H, d, J=5.1 Hz, 1-H), 4.42 (1H, dd, J=7.4, 9.0 Hz, 2-H), 4.01 (1H, dd, J=9.0, 10.6 Hz, 11α-H), 3.80 (6H, s, 3',5'-OCH$_3$), 3.33 (1H, m, 3-H)), 3.20 (1H, dd, J=8.6, 13.7 Hz, 11β-H).

Synthesis of Compounds 102 and 135

Each of these two compounds was synthesized as followed. Reaction of an amino substituted heteroaryl carboxylate with a reducing reagent, e.g., lithium aluminum hydride (1.3–2.0 eq), in a solvent of ether and tetrohydrofuran (3:1) yielded an alcohol as shown in Scheme 5. The resulting alcohol then reacted with DBD to give the desired compound.

Analytical data on Compound 102 are shown below.

Compound 102, i.e., 4'-O-demethyl-4β-[2 "-(4"-hydroxylethyl)-thiazolylamino]-desoxypodophyllotoxin. Amorphous, mp 128° C. (soften) 155–8° C. (dec); ESI MS: 526.2 (M–H); $^1$H NMR (Bruker 400 MHz, CD$_3$OD): δ 6.82 (s, 1H, 5-H), 6.49 (s, 1H, 8-H), 6.32 (s, 2H, 2', 6'-H), 6.24 (s, 1H, 5"-H), 5.92 (d, J=2.0 Hz, 2H, OCH$_2$O), 5.20 (d, J=4.3 Hz, 1H, 4-H), 4.56 (d, J=5.1 Hz, 1H, 1-H), 4.39 (t, J=7.4 Hz, 1H, 11-H), 3.89 (t, J=8.9 Hz, 1H, 11-H), 3.80 (t, J=6.6 Hz, 2H, —CH$_2$CH$_2$OH), 3.71 (s, 6H, 3', 5'-OCH3), 3.15 (dd, J=5.1, 14.5 Hz, 1H, 2-H), 3.04 (m, 1H, 3-H), 2.74 (t, J=6.6 Hz, 2H, —CH$_2$CH$_2$OH).

Synthesis of Compounds 107 141, 142, and 148

Each of Compounds 107 and 148 was synthesized as shown in Scheme 6. A chloro and nitro substituted heteroaryl was treated with a substituted amine (2 eq) in carbon tetrachloride. The reaction solution was heated to reflux for 24 h. The resulting compound as yellow crystal was further refluxed in a mixture of methanol and water with 10% glacial acetic acid for 1 to 2 h in the presence of iron powder to give an amino substituted heteroaryl intermediate. Reaction of the intermediate with DBD yielded the desired product.

Each of Compounds 141 and 142 was synthesized as follows. A chloro and nitro substituted heteroaryl reacted with an alcohol in the presence of sodium to give an ether. The nitro group of the resulting ether was reduced with iron powder to give an amine compound which reacted with DBD to yield the desired product.

Analytical data on Compound 107 are shown below.

Compound 107, i.e., 4'-O-demethyl-4β-[4"-(2"-N,N-diethyl)-pyridylamino]-desoxypodophyllotoxin. Amorphous, mp 92° C. (shrunken) 140–142° C. (melted); ESI MS: 546.4 (M–H); $^1$H NMR (Bruker 400 MHz, CDCl$_3$): δ 7.61 (s, 1H, 6"-H), 6.71 (s, 1H, 4"-H), 6.52 (s, 2H, 3"-H, 5-H), 6.39 (s, 1H, 8-H), 6.34 (s, 2H, 2', 6'-H), 5.96 (dd, J=1.2, 6.7 Hz, 2H, OCH$_2$O), 4.59 (d, J=5.1 Hz, 1H, 1-H), 4.51 (t, J=7.4 Hz, 1H, 11-H), 4.42 (t, J=8.6 Hz, 1H, 4-H), 4.05 (t, J=8.9 Hz, 1H, 11-H), 3.80 (s, 6H, 3', 5'-OCH3), 3.46 (m, 4H, —N(CH$_2$CH$_3$)$_2$), 3.16 (m, 1H, 2-H), 2.99 (m, 1H, 3-H), 1.18 (m, 6H, —N(CH$_2$CH$_3$)$_2$).

Scheme 5
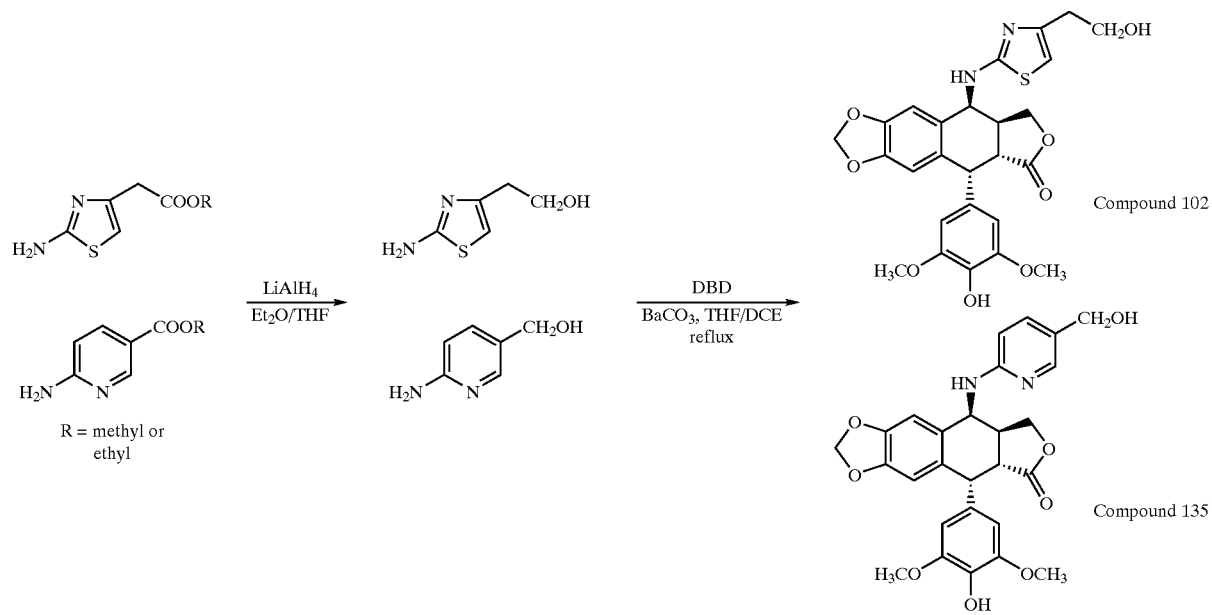
Scheme 6
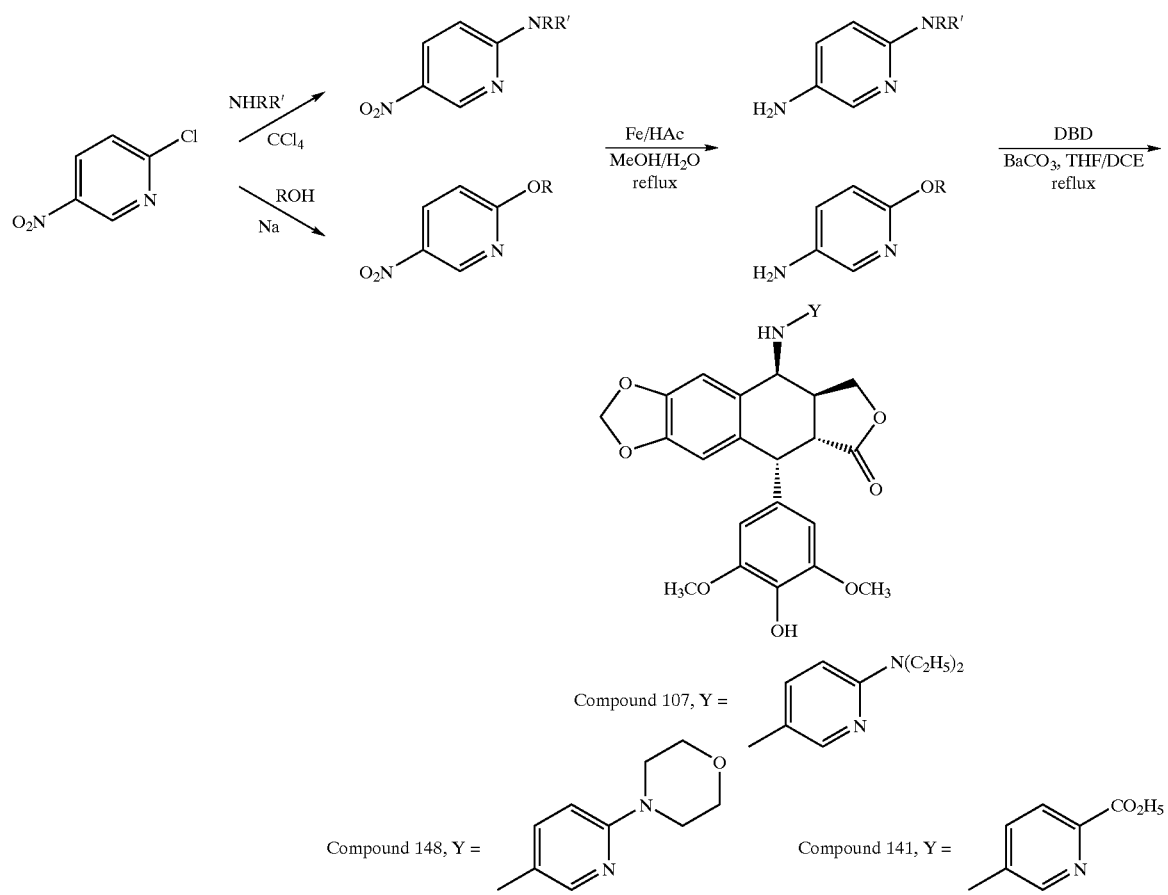

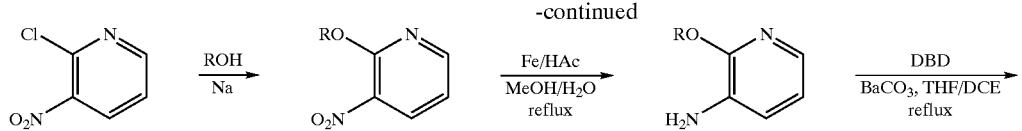

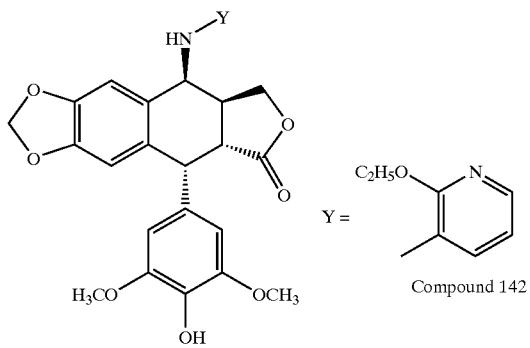

Synthesis of Compounds 159, 179, 189, 190, and 191

Compound 159 was synthesized as shown in Scheme 7. Reaction of 5-amino-3-methyl isothiazole hydrochloride (2 mmol) with bromine (2 mmol) in a solution of 5% glacial acetic acid in benzene (5 mL) at 10° C. provided a solid product as a hydrobromide salt. The solid product was converted to a free base product by stirring with 2N sodium carbonate (D. Buttimore et al. (1963) *JACS* 2032–2039). Reaction the resulting compound with DBD under $N_2$ with refluxing yielded the desired product.

Compounds 179 and 189 were synthesized as shown Scheme 7. Reaction of 5-amino-3-methylisothiazole hydrochloride with acetic chloride in pyridine followed by nitration and reduction gave an intermediate of 4-amino-5-acetamido-3-methylisothiazole. Reaction of the intermediate (1.2 eq ) with DBD under $N_2$ afforded Compound 179. Refluxing 4-nitro-5-acetamido-3-methylisothiazole in 4N HCl aq. and further reacting with DBD under $N_2$ with refluxing yielded Compound 189.

Each of Compounds 190 and 191 was synthesized as shown in Scheme 7. Reaction of 5-amino-3-methylisothiazole hydrochloride with a substituted acetic chloride (2 eq) in pyridine at room temperature, followed by nitration of the resulting compound, 5-dichloroacetamido-3-methylisothiazole, in fuming nitric acid (1.1 eq) and concentrated sulfuric acid at 0° C. gave a nitro compound. Reduction of the nitro compound with iron powder afforded an amino compound. Reaction of the resulting amino compound with DBD afforded the desired product.

Analytical data on Compound 190 are shown below.

Compound 190, i.e., 4'-O-demethyl-4β-[4"-(5"-chloroacetamido-3"-methyl)-isothiazolylamino]-desoxypodophyllotoxin. Amorphous, mp 178–180° C. (dec); ESI MS: 586.2 (M–H); $^1$H NMR (Bruker 400 MHz, $CD_3OD$): δ 6.54 (s, 1H, 5-H), 6.25 (s, 2H, 2', 6'-H), 6.12 (d, J=5.9 Hz, 1H, 8-H), 5.91 (m, 2H, $OCH_2O$), 4.68 (d, J=5.5 Hz, 1H, 1H, 1-H), 4.63 (m, 1H, 4-H), 4.47 (t, J=8.2 Hz, 1H, 11-H), 4.21 (t, J=3.9 Hz, 1H, 11-H), 3.76 (s, 6H, 3', 5'-OCH3), 3.45 (m, 2H, —$CH_2$Cl), 3.40 (m, 1H, 2-H), 3.08 (m, 1H, 3-H), 2.31 (s, 3H, 3"-H).

Synthesis of Compounds 200 and 201

Compound 200 was synthesized as shown in Scheme 8. Reaction of α,γ-dichloroacetone (15.9 mmol) with thiourea (15.9 mmol) in dry acetone (8 mL) afforded a white solid. The white solid was collected and stirred in anhydrous ethanol to remove insoluble isothiourea. To the ethanol filtrate, 25–30 mL of hexanes was added with stirring to afford 2-amino-4-chloromethylthiazole hydrochloride as a white crystalline solid. The resulting compound was further reacted with N,N-diethylamine in ethanol and neutralized with 20% sodium hydroxide to gave an intermediate. The intermediate reacted with DBD to yield the desired product.

Compound 201, i.e., 4'-O-demethyl-4β-[2"-(4"-hydroxylmethyl)-thiazolylamino]-desoxypodophyllotoxin was synthesized as follows. 2-amino-4-chloromethylthiazole hydrochloride (42.0 mmol) in 16 mL of water was heated to reflux for 15 min. The rection solution was evaporated to dryness and the residue was redissolved in water and evaporated. The residue was crystallized from ethanol to give an alcohol intermediate. The intermediate further reacted with DBD under reflux condition to afforded the title compound in 35% yield. Amorphous, mp 185–189° C.; ESI MS: 511.2 (M–H); $^1$H NMR (Bruker 400 MHz, $CD_3OD$): δ 6.82 (s, 1H, 5-H), 6.49 (s, 1H, 8-H), 6.43 (s, 1H, 5"-H), 6.32 (s, 2H, 2', 6'-H), 5.92 (d, J=2.7 Hz, 2H, $OCH_2O$), 5.24 (d, J=4.3 Hz, 1H, 4-H), 4.56 (d, J=5.1 Hz, 1H, 1-H). 4.45 (s, 2H, —$CH_2$OH), 4.41 (t, J=7.4 Hz, 1H, 11-H), 3.88 (t, J=8.9 Hz, 1H, 11-H), 3.71 (s, 6H, 3', 5'-OCH3), 3.15 (dd, J=5.1, 14.5 Hz, 1H, 2-H), 3.04 (m, 1H, 3-H).

Scheme 7
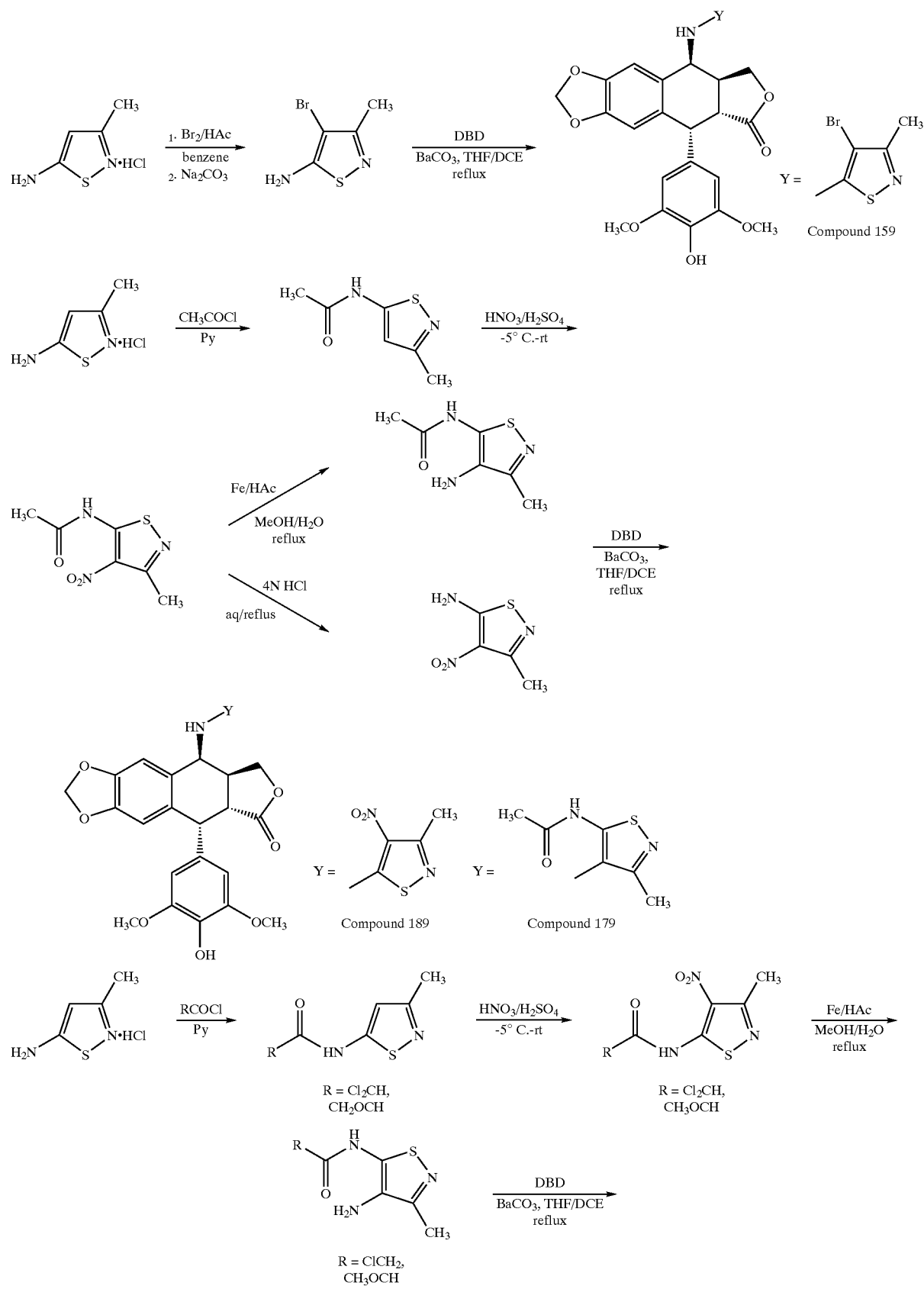

-continued

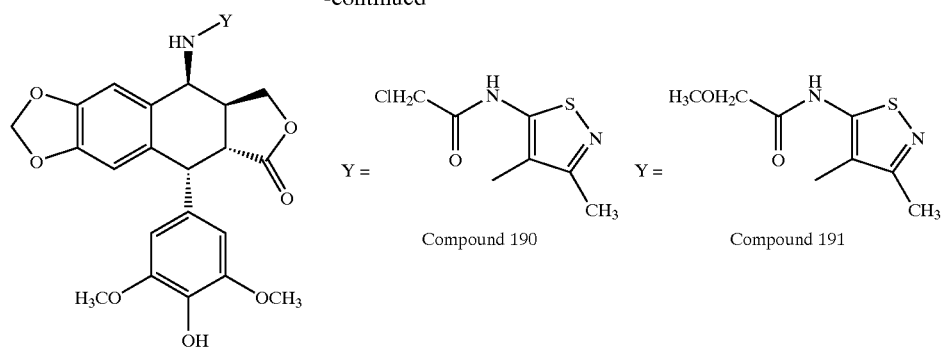

Compound 190  Compound 191

Scheme 8

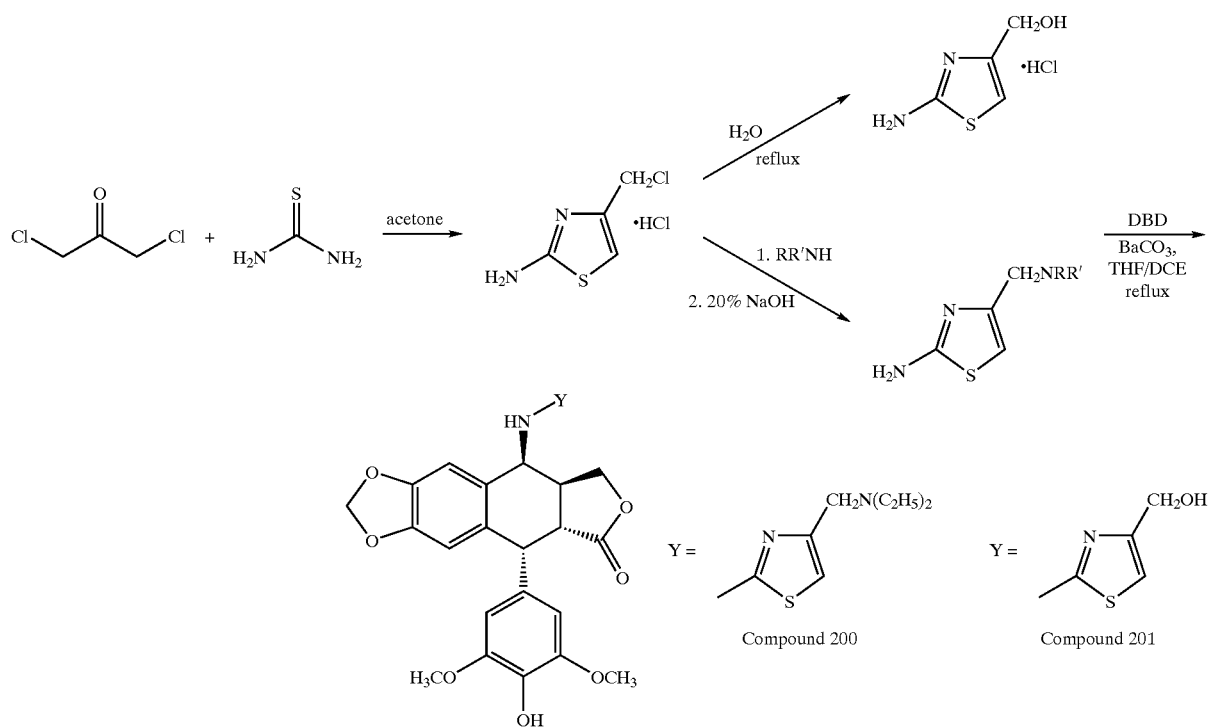

Compound 200  Compound 201

Synthesis of Compounds 207–210

Each of these compounds was synthesized as follows. Reaction of the podophyllotoxin derivatives was treated with phosphorous oxychloride (2 eq for the compounds 207–209, and 4 eq for the compound 210) in the presence of N,N-diisopropylethylamine (5 eq and 10 eq, respectively) at −20 to −15° C. The resulting product was hydrolyzed in water at −5 to 0° C. in the presence of pyridine to provide the desired product.

Analytical data on Compound 210 are shown below.

Compound 210, i.e., 4'-O-demethyl-4β-[2"-(4"-hydroxylethyl)-thiazolylamino]-desoxypodophyllotoxin-4'-O,4"O-diphosphate. Amorphous, mp 176° C. (dec); ESI MS: 685.2 (M−H); $^1$H NMR (Bruker 400 MHz, DMSO-$d_6$): δ 6.88 (s, 1H, 5-H), 6.52 (s, 1H, 8-H), 6.32 (s, 1H, 5"-H), 6.22 (s, 2H, 2', 6'-H), 5.98 (d, J=4.70 Hz, 2H, OCH$_2$O), 5.28 (d, J=4.7 Hz, 1H, 4-H), 4.52 (d, J=5.1 Hz, 1H, 1-H), 4.34 (t, J=7.4 Hz, 1H, 11-H), 3.92 (m, 2H, —CH$_2$CH$_2$OPO$_3$H$_2$), 3.78 (t, J=8.6 Hz, 1H, 11-H), 3.58 (s, 6H, 3', 5'-OCH$_3$), 2.72 (m, 1H, 2-H), 2.67 (m, 1H, 3-H), 2.33 (t, J=2.0 Hz, 2H, —CH$_2$CH$_2$O PO$_3$H$_2$).

Biological Assays

A number of compounds of this invention were evaluated for cytotoxicity against KB cells, which are nasopharyngeal carcinoma cells. They were also tested for stimulation of cellular protein-linked DNA breaks (PLDB) using etoposide as a positive control. Etopside is a widely-used antineoplastic agent, see, e.g., Zhang et al. (1994) *J. Med. Chem.* 37: 446.

Among the tested compounds, Compounds 1, 15, 36, 39, 45, and 49 showed unexpectedly low IC$_{50}$ values against KB cells and are therefore strong cytotoxic agents against cancer cells. Indeed, Compounds 1, 36, 39 and 49 showed unexpectedly high levels of PLDB induction in KB cells when tested at 5 μg/ml.

Three compounds, i.e., Compounds 1, 12, and 38, were also assayed for inhibition of tubulin polymerization in vitro. The results showed that none of them inhibited tubulin

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous podophyllotoxin derivatives of this invention also can be made, screened for their anticancer activities, and used to practice this invention. Thus, other embodiments are also within the claims.

What is claimed is:

1. A compound of formula (I):

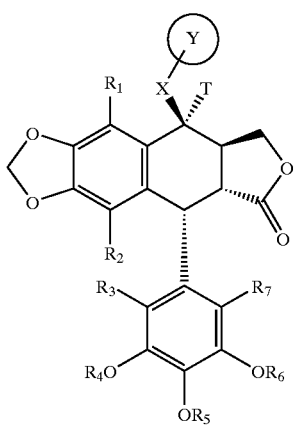

(I)

wherein each of $R_1$, $R_2$, $R_3$ and $R_7$ independently is H or alkyl;
each of $R_4$ and $R_6$ independently is alkyl;
$R_5$ is H or $P(O)(OR_a)_2$, in which $R_a$ is H or alkyl;
T is H, or together with X is =N;
X is a bond, O, S, or $NR_b$, in which $R_b$ is H or alkyl; or together with T, is =N; and
Y is 5-membered heteroaryl or heterocyclyl, optionally substituted with one or more of halogen, alkyl, cyclyl, aryl, heteroaryl, heterocyclyl, —$OR_c$, —$NR_cR_c'$, —$SR_c$, —CN, —$NO_2$, —$SO_2R_c$, —$C(O)OR_c$, —$C(O)NR_cR_c'$, —$NHC(O)R_c$, —$(CH_2)_qOPO_3H_2$, —$CH_2C(O)NOR_c''$, and

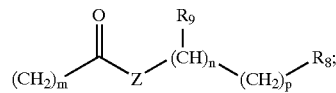

in which each of $R_c$ and $R_c'$ independently is H or alkyl; Rc" is H, alkyl, or silyl; Z is O or NH; each of m and n independently is 0 or 1; p is 0, 1, or 2; q is 1, 2, 3, or 4; and each of $R_8$ and $R_9$ independently is H, alkyl, aryl, heteroaryl, heterocyclyl, —$OR_d$, —$NR_dR_d'$, —$SR_d$, —CN, —$NO_2$, —$SO_2R_d$, —$C(O)OR_d$, —$C(O)NR_dR_d'$, —$NHC(O)R_d$, or —$NHC(O)OR_d$, in which each of $R_d$ and $R_d'$ independently is H or alkyl.

2. The compound of claim 1, wherein X is NH, and T is H.

3. The compound of claim 2, wherein each of $R_1$, $R_2$, $R_3$, and $R_7$ is H.

4. The compound of claim 3, wherein $R_5$ is H.

5. The compound of claim 3, wherein $R_5$ is $P(O)(OH)_2$.

6. The compound of claim 3, wherein each of $R_4$ and $R_6$ is methyl.

7. The compound of claim 6, wherein $R_5$ is H.

8. The compound of claim 7, wherein Y is 5-membered heteroaryl.

9. The compound of claim 8, wherein Y is

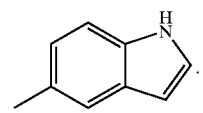

10. The compound of claim 8, wherein Y is 5-membered heteroaryl containing two to four ring heteroatoms.

11. The compound of claim 10, wherein Y is

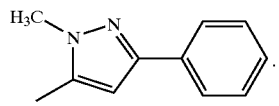

12. The compound of claim 10, wherein Y is

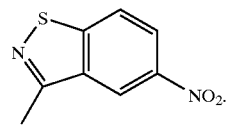

13. The compound of claim 10, wherein Y is

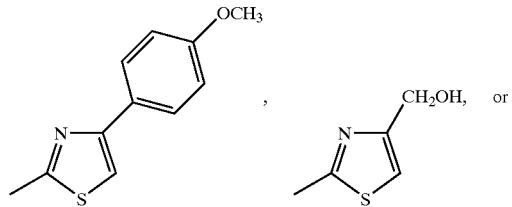

-continued

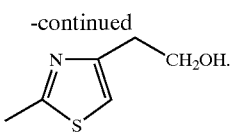

14. The compound of claim 10, wherein Y is

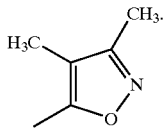

15. The compound of claim 10, wherein Y is

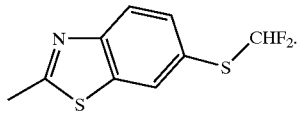

16. The compound of claim 10, wherein Y is

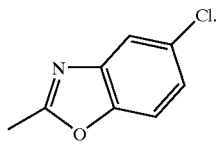

17. The compound of claim 10 wherein Y is

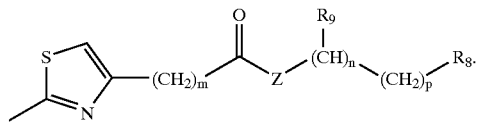

18. The compound of claim 17, wherein m is 1.
19. The compound of claim 18, wherein n is 0.
20. The compound of claim 19, wherein Z is O.
21. The compound of claim 18, wherein n is 1.
22. The compound of claim 21, wherein $R_9$ is C(O)OR$_d$.
23. The compound of claim 22, wherein Z is O.
24. The compound of claim 17, wherein m is 0.
25. The compound of claim 7, wherein Y is 5-membered heterocyclyl.
26. The compound of claim 2, wherein each of $R_4$ and $R_6$ is methyl.
27. The compound of claim 1, wherein X and T together are =N.
28. The compound of claim 27, wherein each of $R_1$, $R_2$, $R_3$, and $R_7$ is H.
29. The compound of claim 28, wherein each of $R_4$ and $R_6$ is methyl.
30. The compound of claim 29, wherein $R_5$ is H.
31. The compound of claim 28, wherein $R_5$ is H.
32. The compound of claim 27, wherein each of $R_4$ and $R_6$ is methyl.

33. A method for treating cancer, comprising administering to a subject in need thereof an effective amount of a compound of formula (I):

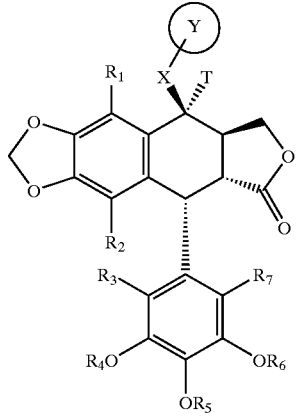

(I)

wherein each of $R_1$, $R_2$, $R_3$ and $R_7$ independently is H or alkyl;

each of $R_4$ and $R_6$ independently is alkyl;

$R_5$ is H or P(O)(OR$_a$)$_2$, in which $R_a$ is H or alkyl;

T is H, or together with X is =N;

X is a bond, O, S, or NR$_b$, in which $R_b$ is H or alkyl; or together with T, is =N; and Y is 5-membered heteroaryl or heterocyclyl, optionally substituted with one or more of halogen, alkyl, cyclyl, aryl, heteroaryl, heterocyclyl, —OR$_c$, —NR$_c$R$_c$', —SR$_c$, —CN, —NO$_2$, —SO$_2$R$_c$, —C(O)OR$_c$, —C(O)NR$_c$R$_c$', —NHC(O)R$_c$, —(CH$_2$)$_q$OPO$_3$H$_2$, —CH$_2$C(O)NOR$_c$", and

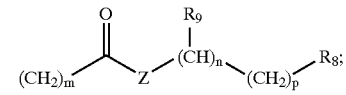

in which each of $R_c$ and $R_c$' independently is H or alkyl; $R_c$" is H, alkyl, or silyl; Z is O or NH; each of m and n independently is 0 or 1; p is 0, 1, or 2; q is 1, 2, 3, or 4; and each of $R_8$ and $R_9$ independently is H, alkyl, aryl, heteroaryl, heterocyclyl, —OR$_d$, —NR$_d$R$_d$', —SR$_d$, —CN, —NO$_2$, —SO$_2$R$_d$—C(O)OR$_d$, —C(O)NR$_d$R$_d$', —NHC(O)R$_d$, or —NHC(O)OR$_d$, in which each of $R_d$ and $R_d$' independently is H or alkyl.

34. The method of claim 33, wherein X is NH, and T is H.
35. The compound of claim 34, wherein each of $R_4$ and $R_6$ is methyl.
36. The compound of claim 34, wherein each of $R_1$, $R_2$, $R_3$, and $R_7$ is H.
37. The compound of claim 36, wherein $R_5$ is H.
38. The compound of claim 36, wherein $R_5$ is P(O)(OH)$_2$.
39. The compound of claim 36, wherein each of $R_4$ and $R_6$ is methyl.

40. The compound of claim 39, wherein $R_5$ is H.
41. The compound of claim 40, wherein Y is 5-membered heteroaryl.
42. The compound of claim 41, wherein Y is
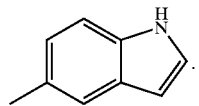
43. The compound of claim 41, wherein Y is 5-membered heteroaryl containing two to four ring heteroatoms.
44. The method of claim 43, wherein Y is
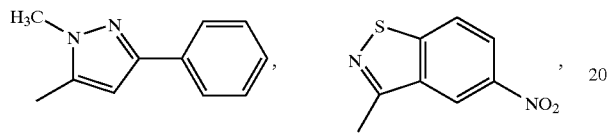
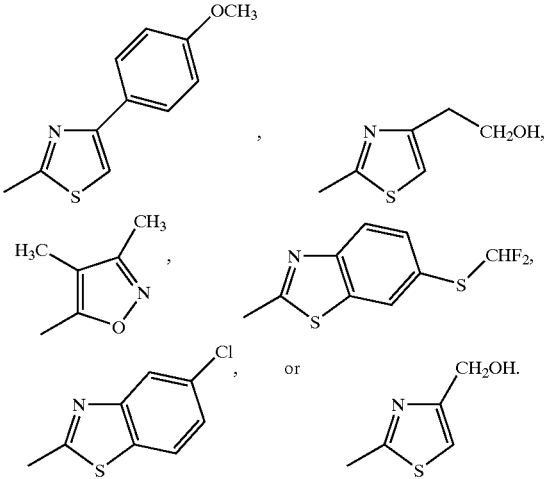
* * * * *